(12) United States Patent
Zalipsky et al.

(10) Patent No.: US 7,108,863 B2
(45) Date of Patent: Sep. 19, 2006

(54) LIPOSOME COMPOSITION FOR IMPROVED INTRACELLULAR DELIVERY OF A THERAPEUTIC AGENT

(75) Inventors: Samuel Zalipsky, Redwood City, CA (US); Theresa M. Allen, Edmonton (CA); Shi Kun Huang, Castro Valley, CA (US)

(73) Assignee: Alza Corporation, Mountain View, CA (US)

( * ) Notice: Subject to any disclaimer, the term of this patent is extended or adjusted under 35 U.S.C. 154(b) by 393 days.

(21) Appl. No.: 10/108,154

(22) Filed: Mar. 26, 2002

(65) Prior Publication Data

US 2002/0192275 A1 Dec. 19, 2002

Related U.S. Application Data

(60) Provisional application No. 60/278,869, filed on Mar. 26, 2001.

(51) Int. Cl.
  *A61B 5/055* (2006.01)
  *A61B 8/00* (2006.01)
  *A61K 9/127* (2006.01)

(52) U.S. Cl. ............... 424/450; 424/9.321; 424/9.51; 424/450

(58) Field of Classification Search ............... 424/450, 424/417, 1.21, 9.321, 9.51; 428/402.2
See application file for complete search history.

(56) References Cited

U.S. PATENT DOCUMENTS

| | | | |
|---|---|---|---|
| 4,235,871 A | 11/1980 | Papahadjopoulos et al. | |
| 5,192,549 A | 3/1993 | Barenolz et al. | |
| 5,620,689 A * | 4/1997 | Allen et al. | 424/178.1 |
| 5,643,599 A | 7/1997 | Lee et al. | |
| 5,891,468 A * | 4/1999 | Martin et al. | 424/450 |
| 5,908,777 A * | 6/1999 | Lee et al. | 435/320.1 |
| 6,056,973 A | 5/2000 | Allen et al. | |
| 6,143,321 A | 11/2000 | Needham et al. | |
| 6,326,353 B1 | 12/2001 | Zalipsky et al. | |

FOREIGN PATENT DOCUMENTS

| WO | WO 00/64484 | 4/2000 |
|---|---|---|
| WO | WO 00/64483 | 11/2000 |

OTHER PUBLICATIONS

S. Zalipsky et al., "New Detachable Poly(ethylene glycol) Conjugates," Bioconjugate Chemistry, American Chemical Society, vol. 10 (No. 5), p. 703-707, (Mar. 26, 1999).

Chen-Yen Wang et al., "pH-sensitive immunoliposomes mediate target-cell-specific . . . ," Proc. Natl. Acad. Sci. USA, p. 7851-7855, (Nov. 26, 1987).

Dexi Liu and Leaf Huang, "Role of cholesterol in the stability of pH-sensitive . . . ," Biochimica et Biophysica Acta, Elsevier, p. 254-260, (Mar. 26, 1989).

Vladimir A. Slepushkin et al., "Sterically Stabilized pH-sensitive Liposomes," Jrl. of Biological Chem., vol. 272 (No. 4), p. 2382-2388, (Mar. 26, 1997).

(Continued)

*Primary Examiner*—S. Tran

(57) ABSTRACT

A liposomal composition and a method of using the same for achieving intracellular delivery of a liposome-entrapped agent is described. The liposomes are composed of a pH sensitive lipid and include a targeting ligand to direct the liposomes to a target cell. The liposomes also include a stabilizing component, such a polymer-derivatized lipid, where the polymer is attached to the lipid by a releasable linkage. Administration of the liposomes results in cellular internalization and destabilization of the liposome for intracellular delivery of the entrapped agent.

23 Claims, 9 Drawing Sheets

OTHER PUBLICATIONS

Dmitri Kirpotin et al., "Liposomes with Detachable polymer coating: ," FEBS Letters, p. 115-118, (Mar. 26, 1996).

Dexi Liu et al., "Characterization of Plasma-Stabilized Liposomes . . . ," Biochemical and Biophysical Res, vol. 162 (No. 1), p. 326-333, (Jul. 14, 1989).

Lee et al., Folate-mediated tumor cell targeting of liposome-entrapped doxorubicin in vito, Biochimica et Biophysica Acta, 1233:134-144, 1995.

Allen et al., Liposomes containing synthetic lipid derivatives of poly(ethylene glycol) show prolonged circulation half-lives in vivo, Biochimica et Biophysia Acta, 1006:29-36, 1991.

Kirchmeier et al., Correlations Between The Rate of Intracellular Pelaase of Endocytosed Liposomal doxorubicin and Cytotoxicity as Determined by a New Assay, Journal of Liposome Research, 11(1), 15-29, 2001.

Lopes De Menezes et al., Cellular Trafficking and Cytotoxicity of Anti-CD19-Targeted Liposomal Doxorubicin in B Lymphoma Cells, Journal of Liposome Research, 9(2), 199-228, 1999.

Lopes De Menezes et al., In Vito and In Vivo Targeting of Immunoliposomal Doxorudicin to Human B-Cell Lymphoma, Cancer Research, 58, 3320-3330, 1998.

Kirpotin et al., Sterically Stabilized Anti-HER2 Immunoliposomes: Design and Targeting to Human Breast Cancer Cells In Vitro, Biochemistry, 36, 66-75, 1997.

Bolotin et al.,Ammonium Sulfate Gradients For Efficient And Stable Remote Loading Of Amphipathic Weak Bases Into Liposomes And Ligandoliposomes, Journal of Liposome Research, 4(1), 455-479, 1994.

Klibanov et al., Long-Circulating Liposomes: Development and Perspectives, Journal of Liposome Research, 2(3), 321-334, 1992.

Litzinger, Phosphatideylethanolamine liposomes: drug delivery, gene transfer and immunodiagnostic applications, Biochimica et Biophysica Acta, 1113, 201-227, 1992.

Zalipsky and Lee, Use of Functionalized Poly (Ethylene Glycol)s for Modification of Polypeptides, Poly(Ethylene Glycol) Chemistry: Biotechnical and Biomedical Applications, Chapter 21, 347-370, 1992.

Zalipsky et al., Evaluation of a New Reagent for Covalent Attachment of Polyethylene Glycol to Proteins, Biotechnology and Applied Biochemistry, 15, 100-114, 1992.

Kaneko et al., New Hydrazone Derivatives of Adriamycin and Their Immunoconjugates-a Correlation between Acid Stability and Cytotoxicity, Bioconjugate Chemistry, 2(3), 133-141, 1991.

Allen et al., Membrane Contact, Fusion, and Hexagonal (Hii) Transition in Phosphatidylethanolamine Liposomes, Biochemistry, 29, 2976-2985, 1990.

Daleke et al., Endocytosos of liposomes by macrophages: binding, acidification and leakages of liposomes monitored by a new fluorescence assay, Biochimica et Biophysia Acta, 1024, 352-366, 1990.

Lui and Huang, Role of Cholesterol in the stability of pH-sensitive, large unilamellar liposomes prepared by the detergent-dialysis method, Biochimica et Biophysica Acta, 981, 254-260, 1989.

Lia et al., Acid-and Calcium-Induced Structral Changes in Phosphatidylethanolamine Membranes Stabilized by Cholesteryl Hemisuccinate, 24, 1654-1661, 1985.

Ellens et al., pH-Induced Destabilization of Phosphalidylethanolamine-Containig Liposomes: Role of Bilayer Contact, Biochemistry, 23, 1532-1538, 1984.

Sommerman et al., I Labelled Inulin: a Convenient Maker for Deposition of Liposomal Contents In Vivo, Biochemical And Biophysical Research Communications, 122(1), 1984.

Mosmann, Rapid Colorimetric Assay for Cellular Growth and Survival: Application to Proliferation and Cytotoxicity Assays, Journal of Immunological Methods, 65, 55-63, 1983.

Tycko et al., Rapid Acidification of Endocytic Vesicles Containing Asialogycoprotein in Cells of a Human Hepatoma Line, The Journal of Cell Biology, 97, 1762-1776, 1983.

Tycko and Maxfield, Rapid Acidification of Endocytic Vesicles Containing $\alpha 2$-Macroglobulin, Cell, 28, 643-651, 1982.

Boris et al., A New Pathway to Unsymmetrical Disulfides. The Thiol-Induced Fragmentation of Sulfenyl Thiocarbonates, Journal of the American Chemical Society, 92:26, 1970.

Grice and Owen, Cytotoxic Compounds. Part IV. Substituted Benzyl Halides, J. Amer. Chem Soc., 363, 1947-1954, 1963.

Bartlett, Phosphorus assay in Column Chromatography, Bioconjugate Chemistry, 234(3), 466-468, 1959.

International Search Report dated Jul. 19, 2002 for corresponding Appn. PCT/US02/09330.

* cited by examiner

LIPOSOME COMPOSITION FOR IMPROVED INTRACELLULAR DELIVERY OF A THERAPEUTIC AGENT

This application claims the benefit of U.S. Provisional Application No. 60/278,869 filed Mar. 26, 2001, which is incorporated herein by reference in its entirety.

FIELD OF INVENTION

The present invention relates to liposomal compositions designed for improved intracellular delivery of an entrapped agent. More specifically, the invention relates to compositions and methods for increasing the intracellular cytotoxicity of a liposome-entrapped agent.

BACKGROUND OF THE INVENTION

Liposomes have long been considered possible vehicles for delivery of therapeutic agents intracellularly. To date, however, success in achieving intracellular delivery of a liposome-entrapped agent has been limited for a variety of reasons. One reason is that liposomes, after systemic administration to the bloodstream, are rapidly removed from circulation by the reticuloendothelial system. Another reason is the inherent difficulty in delivering a molecule, in particular a large or a charged molecule, into the cellular cytoplasm and/or the nucleus.

One approach to improving intracellular delivery of liposome-entrapped agents is to extend the blood circulation lifetime of the liposome by including polyethyleneglycol (PEG) derivatized lipids in the liposome bilayer membrane (see, for example, U.S. Pat. No. 5,013,556). By extending the length of time that the liposomes remain in the bloodstream, the opportunity for uptake by a cell improves.

Another approach to improving intracellular delivery of liposome-entrapped agents is to provide a targeting moiety or ligand on the liposome (Klibanov et al., *J. Liposome Res.*, 2(3):321 (1992)). Binding of the targeting moiety to a receptor on a target cell improves the chance of intracellular uptake of the liposome and its entrapped agent.

Also described in the art are liposomes capable of fusion with a target cell (U.S. Pat. No. 5,891,468). Fusogenic liposomes typically include a hydrophobic segment extending from the liposomes' outer surfaces for penetration into a target cell membrane.

Liposomes that destabilize under mildly acidic conditions, so-called 'pH-sensitive' liposomes, have also been described as an approach to intracellular delivery of an entrapped agent (Slepushkin et al., *J. Biol. Chem.*, 272(4): 2382 (1997); Wang et al., *Proc. Natl. Acad. Sci.*, 84:7851 (1987), Liu et al., *Biochim. Biophys. Acta*, 981:254 (1989)). These liposomes are primarily composed of a lipid, such as dioleoylphosphatidylethanolamie (DOPE), that forms a lipid bilayer in a defined pH range. Outside this pH range, the lipid bilayer destabilizes. After such liposomes enter cells via endocytosis, the acidic pH inside the endosomes causes the pH-sensitive liposomes to destabilize and release the entrapped agent.

Because pH-sensitive liposomes, like "conventional", "non-pH-sensitive liposomes", have short circulation lifetimes, addition of PEG-derivatized lipids to extend the blood circulation time has been proposed (Slepushkin et al.). However, addition of PEG-derivatized lipids attenuates the pH-sensitivity of the liposomes, resulting in a loss of the desired rapid destabilization of the liposome bilayer and accompanying rapid release of the entrapped agent into the cell.

One approach to providing pH-sensitive liposomes having a long blood circulation lifetime and retaining the ability of the liposome to rapidly destabilize is the use PEG-derivatized lipids where the PEG is attached to the lipid by a chemically-cleavable linkage, such as a disulfide (Kirpotin et al., *FEBS Letters*, 388:115 (1996)). It is desirable, however, that the destabilization occurs in the cell to achieve a high intracellular concentration of the liposome-entrapped agent. The long-circulating, pH-sensitive liposomes described by Kirpotin et al. (Id.) were designed to destabilize extracellularly by release of the PEG chains. This approach suffers from the disadvantage of releasing the entrapped liposome contents extracellularly.

Accordingly, there remains a need in the art for a liposome composition capable of specific binding to a target cell accompanied by rapid intracellular release of its entrapped agent.

SUMMARY OF THE INVENTION

Accordingly, it is an object of the invention to provide a liposome composition capable of intracellular delivery of a liposome-entrapped agent.

It is a further object of the invention to provide a liposomal composition and a method of using the same to treat a variety of disorders, and in particular to treat haematological malignancies.

Accordingly, in one aspect the invention includes a liposome composition for intracellular delivery of a therapeutic agent. The composition is comprised of liposomes formed of (i) a pH-sensitive lipid; (ii) between 1–20 mole percent of a lipid derivatized with a hydrophilic polymer, the polymer attached to the lipid by a bond effective to release the hydrophilic polymer chains in response to an existing or an induced physiologic condition; (iii) a targeting ligand; and (iv) an entrapped therapeutic agent. The composition is effective to bind to a target cell and to release the entrapped agent to achieve at least a two-fold increase in intracellular concentration of the drug, when compared to intracellular concentration of the drug delivered by similar liposomes lacking the releasable bond and/or the targeting ligand.

In one embodiment, the pH-sensitive lipid is dioleoylphosphatidylethanolmaine (DOPE). In another embodiment, the liposomes further include a stabilizing component, such as cholesteryl hemisuccinate (CHEMS).

The lipid derivatized polymer, in one embodiment, is phosphatidylethanolamine derivatized with polyethyleneglycol. The targeting ligand can be an antibody or an antibody fragment, and for treatment of certain disorders the antibodies or fragments from the antibodies anti-CD19, anti-CD20, or anti-CD22 are preferred.

The releasable bond that joins the hydrophilic polymer chain to the lipid, in one embodiment, contains a disulfide bond. The disulfide bond, in a preferred embodiment, is part of a dithiobenzyl bond.

In another aspect, the invention includes a method for increasing intracellular cytotoxicity of a liposome-entrapped agent. The method includes providing liposomes having the composition described above, and administering the liposomes to achieve (i) cleavage of the releasable bond, thereby releasing the hydrophilic polymer chain; (ii) binding of the ligand to a target cell, where the binding occurs prior to or subsequent to the cleavage; and (iii) internalization of the liposome by the target cell. Such administering is effective to achieve at least a two-fold higher intracellular cytotoxicity of the agent, relative to intracellular concentration of the drug delivered by similar liposomes lacking the releasable bond and/or the targeting ligand.

In one embodiment, cleavage of the releasable bond after administering the composition is achieved by one or more endogeneous agents, such as a component naturally-occurring in the blood or in a cell.

In another aspect, the invention relates to a method for increasing accumulation of a therapeutic agent in cellular nuclei by providing liposomes as described above and administering the liposomes to achieve (i) cleavage of the releasable bond, thereby releasing all or a portion of the hydrophilic polymer chains; (ii) binding of the ligand to a target cell, where the binding occurs prior to or subsequent to the cleavage; and (iii) internalization of the liposome by the target cell. Such administering is effective to achieve at least a two-fold higher accumulation of the agent in the nucleus of the target cell, when compared to intracellular concentration of the agent delivered by similar liposomes lacking the releasable bond and/or the targeting ligand.

These and other objects and features of the invention will be more fully appreciated when the following detailed description of the invention is read in conjunction with the accompanying drawings.

DETAILED DESCRIPTION OF THE INVENTION

Figure 1A:
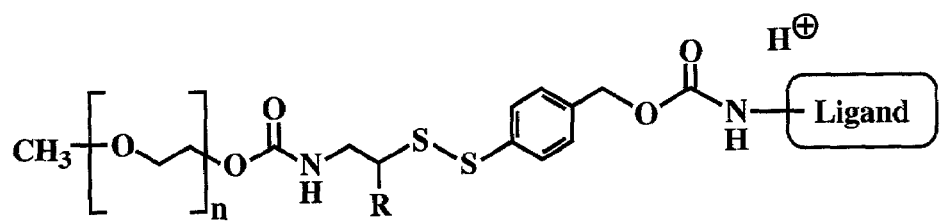
FIG. 1A shows an embodiment of the invention where the dithiobenzyl (DTB) links a methoxy-polyethyelene glycol (mPEG) moiety and the amine-containing ligand.

The present invention provides liposomal compositions and methods using the same for intracellular delivery of a liposome-entrapped agent. The liposomes are adapted to rapidly release the entrapped agent in response to a below physiological pH environment at a target site, such as the internal region of a cell or an intracellular organelle. Below, the liposome composition is described and intracellular delivery of the liposomal contents is shown.

Definitions and Abbreviations

"An induced physiologic condition" refers to an exogenous agent or condition, such as heat, light, a chemical agent, or biological agent, administered to a subject treated with the liposomes described herein, where the agent or condition is effective to cause cleavage of a labile bond.

"An existing physiologic condition" refers to an endogenous agent or condition, such a chemical agent, a biological agent, a pH level, or a temperature, effective to cause cleavage of a labile bond.

The phrase "effective to release the hydrophilic polymer chains" intends release of all or at least a portion of the polymer chains.

A "pH-sensitive" lipid refers to a lipid whose ability to form and/or maintain formation of a lipid bilayer depends at least in part on the pH of the surrounding environment.

DOPE refers to dioleoylphosphatidylethanolamine.
DSPE refers to distearoylphosphatidylethanolamine.
mPEG-DSPE refers to methoxypoly(ethylene glycol) covalently coupled to DSPE.
mPEG-S-S-DSPE refers to N-[2-ω-methoxypoly(ethylene glycol)-α-aminocarbonylethyl-dithiopropionyl]-DSPE.
Mal-PEG-DSPE refers to maleimide-terminated polyethylene glycol covalently coupled to DSPE.
CHEMS refers to cholesteryl hemisuccinate.
CFE refers to cell free extract.
mAb refers to monoclonal antibody.
DXR refers to doxorubicin.
HPTS refers to trisodium 8-hydroxypyrenetrisulfonate.
HSCP refers to hydrogenated soy phosphatidylcholine.
TI refers to tyraminylinulin.
DPX refers to p-xylene-bis-pyridinium bromide.

Liposome Composition

The liposomes for use in the method of the invention are comprised of a pH-sensitive lipid and of a lipid derivatized with a hydrophilic polymer, where the polymer and the lipid are joined by a cleavable bond. The liposomes also include a ligand or moiety effective to target the liposomes to a specific cell. Entrapped in the liposomes is a therapeutic agent for intracellular delivery. Each of these components will now be described.

pH-sensitive Lipid Component

The liposomes include a pH-sensitive lipid, that is a lipid that forms bilayer vesicles in the absence of a stabilizing component only at specific pH ranges. These lipids are typically amphipathic lipids having hydrophobic and polar head group moieties, and when arranged into a bilayer are oriented such that the hydrophobic moiety is in contact with the interior, hydrophobic region of the bilayer membrane, and the polar head group moiety is oriented toward the exterior, polar surface of the membrane. The pH sensitive amphipathic lipids preferably have two hydrocarbon chains, typically acyl chains between about 8–22 carbon atoms in length, and have varying degrees of unsaturation.

A preferred pH sensitive lipid is dioleoylphosphatidyl ethanolamine (DOPE), a phospholipid having diacyl chains. At physiological pH and ionic strengths, DOPE exists in an inverted hexagonal ($H_{II}$) phase incapable of forming bilayers. Bilayer liposomes of DOPE can be made at pHs above the $pK_a$ for the amine group, i.e., about pH of approximately 8.5 (Allen T. M. et al., *Biochemistry*, 23:2976 (1990)). However, at pHs where the acid is negatively charged, DOPE can be stabilized in the bilayer state in the presence of an amphiphile with charge-repulsing hydrophilic moieties (Litzinger, L. H. *Biochim. Biophys. Acta*, 1131:201 (1992); Kirpotin et al., *FEBS Letters*, 388:115 (1996)). Protonation of the amphiphile at the $pK_a$ of the amphilphile accelerates the destabilization of DOPE vesicles by promoting the reversion to the hexagonal phase ($H_{II}$) (Lai, M. Z. et al. *Biochemistry*, 24:1654 (1985); Ellens, H. et al, *Biochemistry*, 23:1532 (1984)). Thus, the pH at which the liposomes will release their contents can be controlled by the selection of the stabilizing amphilphiles.

In one embodiment of the present invention, DOPE is stabilized in the bilayer state by bulky cholesteryl hemisuccinate (CHEMS). CHEMS is net negatively charged at pH 7.4, and stabilizes DOPE in the bilayer state at neutral pH. At pH levels of approximately 6.0 and lower, CHEMS protonates, which results in a destabilization of DOPE vesicles.

DOPE can also be stabilized in the bilayer state at pH range between 5.5–7.4 by the inclusion of a small mole percent of an amphipathic lipid having a bulky hydrophilic moiety, e.g., a PEG-lipid derivative, as will be described below.

Polymer-Derivatized Lipid Component

The liposomes also include a lipid derivatized with a hydrophilic polymer. The polymer derivatized lipids serve to stabilize the pH sensitive lipid to facilitate bilayer, and liposome, formation and to form a coating of polymer chains over the liposome surface to extend the blood circulation lifetime of the liposomes. That is, the hydrophilic polymer coating provides colloidal stability and serves to protect the liposomes from uptake by the mononuclear phagocyte system, providing a longer blood circulation lifetime for the liposomes to distribute in the organism. The polymer chains are attached to the lipid by a releasable bond for cleavage and release of the polymer chains, in order to restore the pH sensitivity of the liposomes, as will be described.

Preferably, the derivatizable lipid is a non-pH sensitive vesicle-forming amphipathic lipid which can spontaneously form into a bilayer vesicle in water. Vesicle-forming lipids of this type are preferably ones having two hydrocarbon chains, typically acyl chains and a head group, either polar or non-polar. There are a variety of synthetic and naturally-occurring vesicle-forming amphipathic lipids, including and not limited to the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and having varying degrees of unsaturation. The above-described lipids and phospholipids whose acyl chains have varying degrees of saturation can be obtained commercially or prepared according to published methods. Preferred diacyl-chain amphipathic lipids for use in the present invention include diacyl glycerol, phosphatidyl ethanolamine (PE) and phosphatidylglycerol (PG), and phosphatidyl ethanolamine (PE) being the most preferred. In one preferred embodiment of the invention, distearolyl phosphatidyl ethanolamine (DSPE) is used.

Hydrophilic polymers suitable for derivatizing the amphipathic lipids include polyvinylpyrrolidone, polyvinylmethylether, polymethyloxazoline, polyethyloxazoline, polyhydroxypropyloxazoline, polyhydroxypropyhnethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

In a preferred embodiment, the hydrophilic polymer is polyethyleneglycol (PEG), preferably as a PEG chain having a molecular weight between 500–10,000 Daltons, more preferably between 2,000–10,000 Daltons, and most preferably between 1,000–5,000 Daltons.

Releasable Linkage

As described above, the hydrophilic polymer is joined to the vesicle-forming lipid through a releasable linkage, that is a linkage that cleaves upon exposure to a particular stimulus, such as heat, a change in pH, or an exogeneously-administered chemical or biological agent. In a preferred embodiment, the linkage is one that responds to a stimulus that is an endogenous, in vivo stimulus, including but not limited to a chemical or biological agent in a cell, blood (plasma), or in the proximity of a target cell surface.

Suitable releasable linkages include, for example, peptide, ester, or disulfide linkages. Ester and peptide linkages can be cleaved by endogenous or exogenous esterase or peptidase enzymes. Disulfide linkages can be cleaved by administration of a reducing agent, such as dithiothreitol (DTT), glutathione or ascorbate, or in vivo by a reducing agent such as cysteine, or reducing enzymes which are present in plasma and intracelluarly.

In a preferred embodiment, the releasable linkage is a disulfide bond, broadly intended herein to refer to sulfur-containing bonds. The sulfur-containing bonds can be synthesized to achieve a selected degree of liability, as known in the art and described, for example, in U.S. Pat. No. 6,043,094. A variable degree of lability permits tailoring the rate of release of the hydrophilic polymer coating from the liposome surface. Generally, when a longer circulation lifetime is needed, a less labile bond is used.

An exemplary disulfide bond is dithiopropionyl (DTP), as described in the art (Kirpotin et al., *FEBS Letters*, 388:115 (1996)). Synthesis of polyethyleneglycol (PEG) linked to the lipid distearolphosphatidylethanolamie (DSPE) by DTP is accomplished by reaction of the succinimidyl ester of dithiobis(succinimidyl propionate) with an excess of mPEG-NH2 to form N-succinimidyl-[2-(methoxypoly(oxyethylene)-α-aminocarbonyl)ethyl-dithiopropiorate, mPEG-DTP-OSu. This is reacted with DSPE to form the desired conjugate, mPEG-DTP-DSPE (Id.).

Another preferred releasable linkage is a dithiobenzyl (DTB) bond (Zalipsky et al, *Bioconjugate Chemistry*, 10(5): 703(1999); WO 00/64483 and WO 00/64484) as has been described in co-pending U.S. application Ser. Nos. 09/556,056 and 09/556,610, both of which are incorporated by reference herein. The linkage is represented by the general structure:

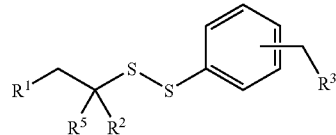

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C{=}O)R^4$, $S(C{=}O)R^4$, and $O(C{=}S)R^4$; $R^4$ comprises an amine-containing lipid, such as the vesicle-forming lipids described above; and $R^5$ is selected from the group consisting of H, alkyl and aryl; and where orientation of $CH_2$—$R^3$ is selected from the ortho position and the para position.

FIG. 1A shows the structure of an exemplary compound in accord with the invention, where $R^1$ is the hydrophilic polymer methoxy-polyetheylene glycol, mPEG=$CH_3O(CH_2CH_2O)_n$ where n is from about 10 to about 2300, which corresponds to molecular weights of about 440 Daltons to about 100,000 Daltons. The molecular weight of the polymer depends to some extent on the selection of $R^3$. In embodiments where $R^3$ is an amine-containing lipid for use in a liposome a preferred range of PEG molecular weight is from about 750 to about 10,000 Daltons, more preferably from about 2,000 to about 5,000 Daltons. The mPEG in this embodiment includes a urethane linking moiety. It will be appreciated that $R^1$ can be selected from a variety of hydrophilic polymers, and exemplary polymers are recited above. It will also be appreciated that the molecular weight of the polymer may depend on the amount of the polymer-DTB-lipid conjugate included in the liposome composition, where a larger molecular weight polymer is often selected when the amount of polymer-DTB-lipid in the composition is small, thus yielding a small number of liposome-attached polymer chains.

With continuing reference to FIG. 1A, $R^2$ and $R^5$ in this exemplary compound are hydrogen (H), however either or both $R^2$ and $R^5$ can also be a straight chain or branched alkyl or an aryl group. In a preferred embodiment, $R^5$ is H and $R^2$ is an alkyl, and several examples are given below. In the compound shown in FIG. 1A, $R^3$ takes the general form of $O(C{=}O)$—($NH_2$-ligand), where the $NH_2$-ligand can be any amine-containing lipid. $R^3$ can also be of the form $O(C{=}S)$—($NH_2$-ligand) or $S(C{=}O)$—($NH_2$-ligand).

Figure 1B:
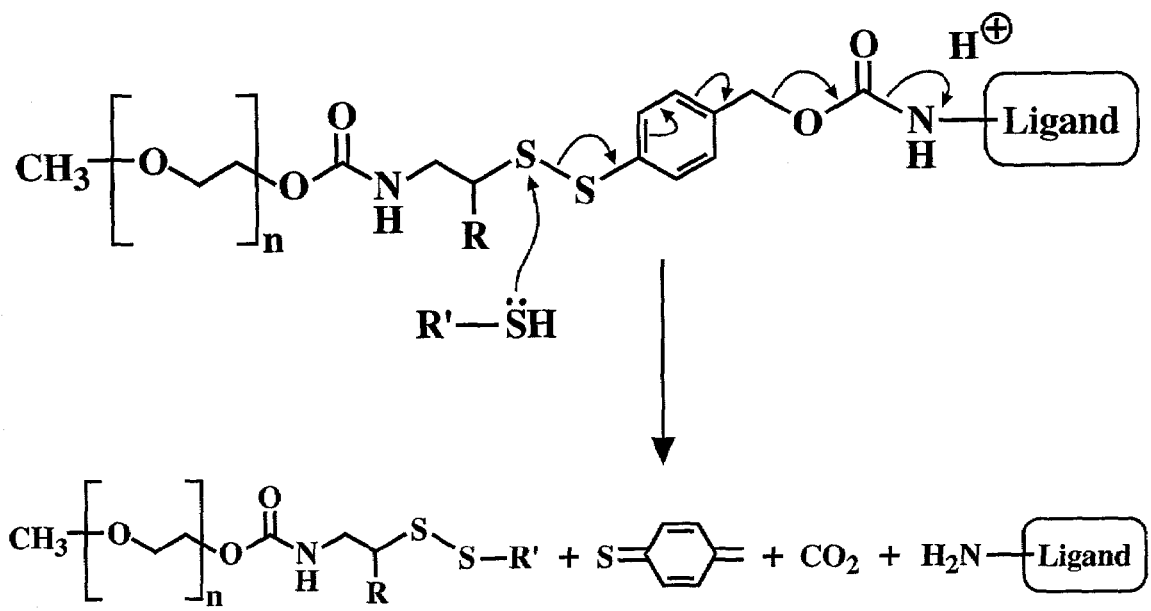
FIG. 1B shows the products after thiolytic cleavage of the compound in FIG. 1A.

FIG. 1B shows the mechanism of thiolytic cleavage of the mpEG-DTB-($NH_2$-lipid) compound of FIG. 1A. The ortho- or para-dithiobenzyl carbamate moiety is cleavable under mild thiolytic conditions, such as in the presence of cysteine or other naturally-occurring reducing agents. Upon cleavage, the amine-containing lipid is regenerated in its natural, unmodified form. Studies in support of the invention, described below, show that natural, physiologic conditions in vivo are sufficient to initiate and achieve cleavage of the DTB linkage. It will be appreciated that a reducing agent can also be administered to artificially induce thiolytic conditions sufficient for cleavage and decomposition of the compound.

Lipids suitable for use in the polymer-DTB-lipid conjugate are preferably water-insoluble molecules having at least one acyl chain containing at least about eight carbon atoms, more preferably an acyl chain containing between about 8–24 carbon atoms. A preferred lipid is a lipid having an amine-containing polar head group and an acyl chain. Exemplary lipids are phospholipids having a single acyl chain, such as stearoylamine, or two acyl chains. Preferred phospholipids with an amine-containing head group include phosphatidylethanolamine and phosphatidylserine. The lipid tail(s) can have between about 12 to about 24 carbon atoms and can be fully saturated or unsaturated. One preferred lipid is distearoylphosphatidylethanolamine (DSPE), however those of skill in the art will appreciate the wide variety of lipids that fall within this description. It will also be appreciated that the lipid can naturally include an amine group or can be derivatized to include an amine group. Other lipid moieties that do not have an acyl tail, such as cholesterolamine, are also suitable.

Figure 2:
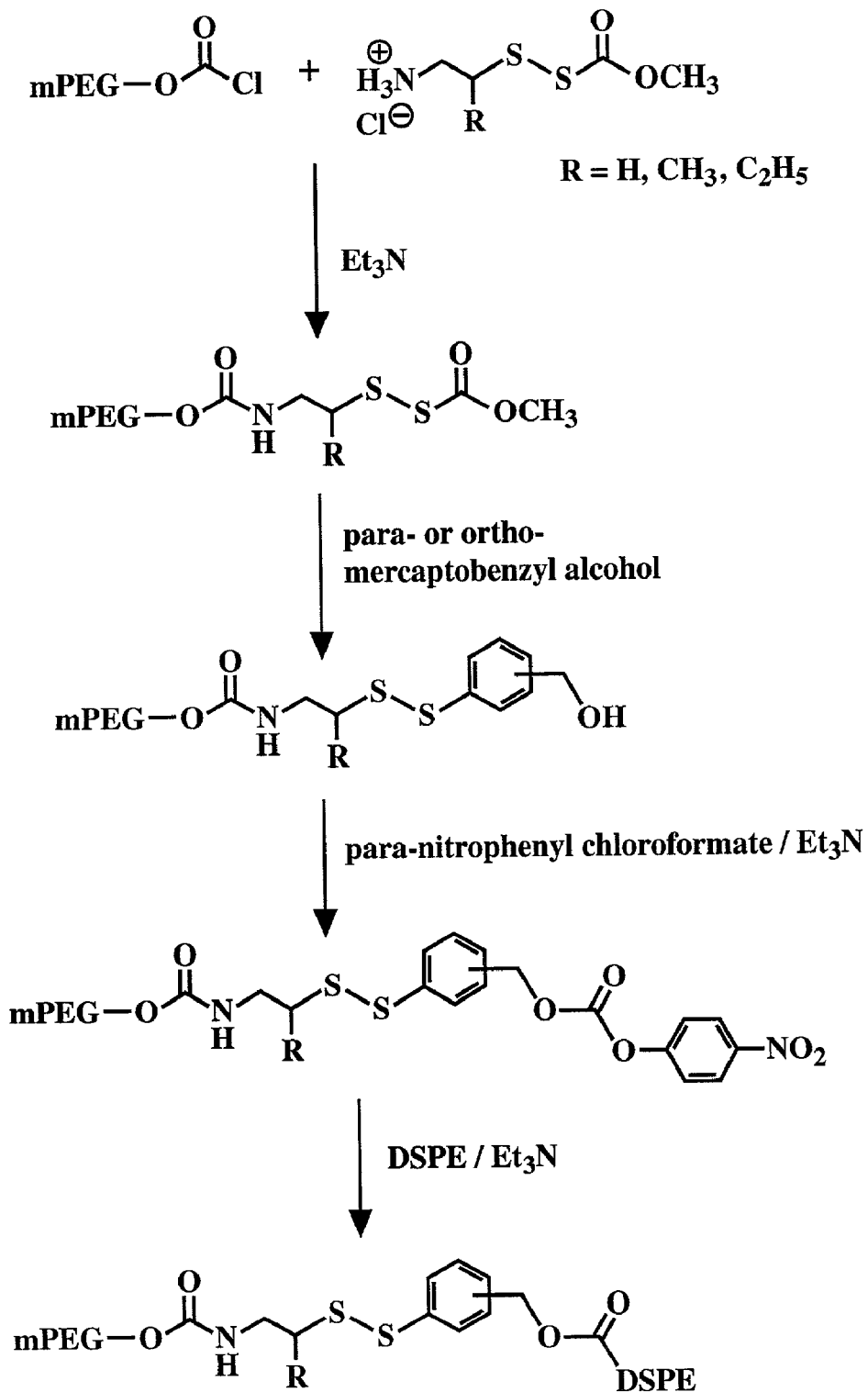
FIG. 2 illustrates a synthetic reaction scheme for synthesis of the mPEG-DTB-amine-lipid, where the amine-lipid is the lipid distearoylphosphatidylethanolamine (DSPE).

The synthesis of a polymer-DTB-lipid compound has been described elsewhere ((Zalipsky et al., Bioconjugate Chemistry, 10(5):703(1999); WO 00/64483 and WO 00/64484) and an exemplary synthetic route is schematically depicted in FIG. 2. mPEG derivatives (MW 2000 and 5000 Daltons) having a methoxycarbonyldithioalkyl end group were prepared by reacting 2-(methoxycarbonyldithio)ethaneamine with mPEG-chloroformate, which was readily prepared by phosgenation of dried mPEG-OH solution (Zalipsky, S., et al., Biotechnol. Appl Biochem. 15:100–114 (1992)). The former compound was obtained through 2-aminoethanethiol hydrochloride reaction with an equivalent amount of methoxycarbonylsulfenyl chloride, according to published procedures (Brois, S. J., et al., J. Amer. Chem. Soc. 92:7629–7631 (1970); Koneko, T., et al., Bioconjugate Chem. 2:133–141 (1991)). Both the para and ortho isomers of mercaptobenzyl alcohol (Grice, R., et al., J. Chem. Soc. 1947–1954 (1963)) coupled cleanly with the resulting PEG-linked acyldisulfide, yielding mPEG bearing a dithio benzyl alcohol end group. Active carbonate introduction proceeded as with underivatized mPEG-OH, to give the para-nitrophenyl carbonate. Addition of DSPE in ethanolamine formed the desired mPEG-DTB-DSPE product. Both ortho- and para-DTB-lipid compounds are prepared by ths method, and can then be purified by silica gel chromatography and characterized by NMR and MALDI-TOFMS.

Figure 3:
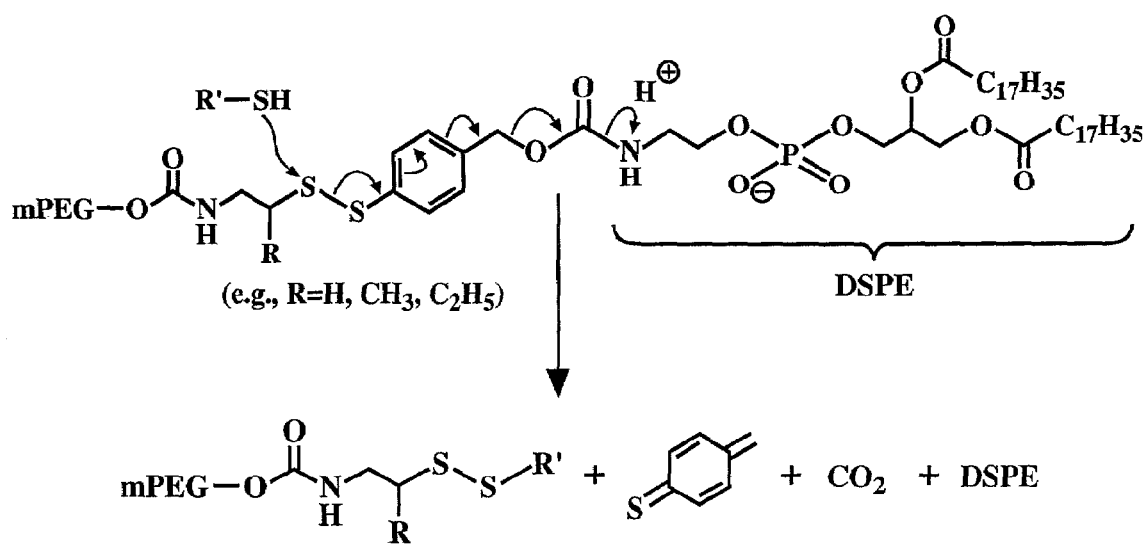
FIG. 3 illustrates the thiolytic cleavage mechanism of a para-dithiobenzyl urethane (DTB)-linked mPEG-DSPE conjugate.

FIG. 3 shows the mechanism of thiolytic cleavage of the mPEG-DTB-DSPE conjugate. Upon cleavage, the phosphatidylethanolamine lipid (DSPE) is regenerated in its natural, unmodified form.

End Functionized Polymer-Lipid Conjugates

The liposome composition of the invention further includes a targeting moiety. In a preferred embodiment, the targeting ligand is covalently attached to the distal end of a liposome-anchored hydrophilic polymer chain. For example, the free distal end of the polymer in the lipid-DTB-polymer described above can be modified to include a terminal reactive group (end-functionalized) adapted to couple with functional groups within the targeting moiety molecules. Such polymer-terminal reactive groups are known in the art, and selected according to the targeting ligand to be attached. For example, where the targeting moiety is an antibody or an antibody fragment, the polymer chains are functionalized to contain reactive groups suitable for coupling with, for example, sulfhydryls, amino groups, and aldehydes or ketones (typically derived from mild oxidation of carbohydrate portions of an antibody) present in the antibody. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive).

Other suitable reactive end groups include malemides and hydrazines. Maleimides are widely used protein modifying reagents and are especially useful when the maleimide is one of two functional groups in a hetero-bifunctional crosslinking reagent. The reaction of maleimides with sulfhydryl groups involves Michael addition of the mercaptan group to the activated double bond. Reaction with amino groups occurs by the same mechanism, but at a much slower rate. Since mercaptan is the most reactive species, particularly at neutral pH, the maleimide group can be used to target sulfhydryl groups in the targeting moiety and good selectivity is usually achieved.

Hydrazide or hydrazine groups are reactive toward aldehyde groups. Hydrazides can also be acylated by active esters or carbodiimide-activated carboxyl groups. Acyl azide groups reactive as acylating species can be easily obtained from hydrazides and permit attachment of amino-containing molecules.

The methods of preparing end-functionalized polymer-lipid conjugates are generally known in the art. For example, co-owned U.S. Pat. No. 5,620,689, disclose the methods of preparing and using maleimide, hydrazide, and 2-pyridyldithio propionamide end groups for coupling of antibodies or antibody fragments to polymer chains; the disclosure of which are incorporated herein by reference.

It will be appreciated that the targeting ligand can also be included in the liposomes by means of a lipid-polymer conjugate with no releasabe linkage joining the lipid and the polymer. It will also be appreciated that any lipids suitable to form the hydrophillic polymer coating of the liposome discussed above may be used to form the modified polymer-lipid conjugate, and any of the hydrophilic polymers described above are suitable. Preferably, in attaching a targeting moiety to a PEG-functionalized lipid, the targeting moiety does not suffer any loss of activity.

The targeting moiety may be attached to a liposome surface by including the end-functionalized polymer-lipid conjugate in the liposome and then after liposome formation, reacting the desired targeting ligand with the reactive polymer ends in the preformed liposome. Alternatively, the ligand-polymer-lipid can be included in the lipid composition at the time of liposome formation. It is also possible to incorporate the ligand-polymer-lipid conjugate into preformed liposomes by insertion, where the ligand-polymer-lipid conjugate is incubated with the preformed liposomes under conditions suitable to allow the conjugate to become incorporated into the liposome lipid bilayer. The insertion technique has been described in the art, for example in U.S. Pat. No. 6,056,973.

Targeting Moiety

A wide variety of targeting moieties are contemplated for use, and exemplary moieties include those set forth, for example, in U.S. Pat. No 5,891,468, and the portions of this patent describing the ligands are incorporated by reference herein. In general, the targeting moiety is a ligand effective to bind specifically with a cell-surface receptor on the target cells.

In a preferred embodiment, the ligand is an antibody or an antibody fragment, targeting antigens specific to a receptor on a target cell. Antibodies can be monoclonal antibodies, or antibody fragments, which are target specific. In a preferred embodiment, the antibodies attached to the liposomes are anti-CD19, anti-CD20, or anti-CD22, for specific binding to a B-cell epitope. These antibodies or antibody fragments are typically derived from hybridomas that show positive reactivity toward the affected B-cells. It is contemplated that other antibodies or antibody fragments targeting any other cell in the body can be similarly used.

In studies performed in support of the present invention, anti-CD19 antibodies were used to target liposome containing an entrapped agent to malignant B-cells. The antibody recognizes a unique epitope, the CD19 surface antigen, on the B-cells. As will be described below, the pH-sensitive liposomes with the targeting moiety were effective to delivery the entrapped agent intracellularly.

Liposome-Entrapped Therapeutic Agent

Entrapped in the liposomes is a therapeutic agent for delivery intracellulary to the target cells. A variety of therapeutic agents can be entrapped in lipid vesicles, including water-soluble agents that can be stably encapsulated in the aqueous compartment of the vesicles, lipophilic compounds that stably partition in the lipid phase of the vesicles, or agents that can be stably attached, e.g., by electrostatic attachment to the outer vesicle surfaces. Exemplary water-soluble compounds include small, water-soluble organic compounds, peptides, proteins, DNA plasmids, oligonucleotides and gene fragments.

The liposome-entrapped compound may also be an imaging agent for tracking progression of a disease. Imaging agents include chelates of radionuclides, such as technetium-99, indium-111, and iodine-125.

The entrapped agent may also be a reporter molecule, such as an enzyme or a fluorophore, for use in in vitro diagnostic assays. Such liposomes having an entrapped reporter molecule may be delivered by fusion to either target cells or receptor-containing liposomes.

In one embodiment, the compound is useful for treatment of a plasma cell disorder, such as multiple myeloma, which is characterized by neoplasms of B-lymphocyte lineage cells. Therapeutic agents preferred for treatment of multiple myeloma include melphalan, cyclophosphamide, prednisone, chlorambucil, carmustine, dexamethasone, doxorubicin, cisplatin, paclitaxel, vincristine, lomustine, and interferon. Typical doses for standard chemotherapy treatment for some of these drugs are as follows: melphalan, 8 mg/m$^2$ body surface area per day; cyclophosphamide, 200 mg/m$^2$ per day; chlorambucil, 8 mg/m$^2$ per day; prednisone 25–60 mg/m$^2$ per day, vincristine (1.4 mg/m$^2$) and doxorubicin (60–75 mg/m$^2$).

Also contemplated is intracytoplasmic delivery of plasmids, antisense oligonucleotides, and ribozymes for the treatment of cancer and viral infections.

In the present invention, the therapeutic agent is entrapped in the liposome, by methods discussed below, for administration parenterally to a subject. The dose used for liposome administration may initially be based on the standard chemotherapeutic dose and adjusted accordingly over the course of treatment by monitoring the disease progression.

Preparation of pH Senisitive, Targeting Liposomes

Liposomes containing an entrapped agent can be prepared according to well-known methods, such as hydration of a lipid film, reverse-phase evaporation, and solvent infusion. The compound to be delivered is either included in the lipid film, in the case of a lipophilic compound, or is included in the hydration medium, in the case of a water-soluble therapeutic agent. Alternatively, the therapeutic agent may be loaded into preformed vesicles, e.g., by loading an ionizable compound against an ion gradient.

One well known procedure for formation of multilamellar vesicles (MLVs) is a simple lipid-film hydration technique. In this procedure, a mixture of liposome-forming lipids are dissolved in a suitable organic solvent which is then evaporated to form a thin lipid film. The lipid film is then hydrated with an aqueous medium to form MLVs, typically with sizes between about 0.1 to 10 microns.

The therapeutic compound to be delivered may be incorporated into liposomes by adding the drug to the vesicle-forming lipids prior to liposome formation, to entrap the drug in the formed liposome. If the drug is hydrophobic, it can be added directly to the hydrophobic mixture, whereas a hydrophilic drug can be added to the aqueous medium which covers the thin film of dried lipids. Alternatively, the drug may be incorporated into preformed liposomes by active transport mechanisms, such as remote loading by which the compound is taken up in liposomes in response to a gradient, such as an ammonium sulfate gradient (U.S. Pat. No. 5,192,549; Bolotin et al., *J. Liposome Res.*, 4:455 (1994)), or a potassium or hydrogen ion concentration.

After formation, the liposomes are sized. One effective sizing method for MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less. In a preferred embodiment of the present invention, the liposomes are extruded through a series of polycarbonate filters with pore sizes ranging from 0.2 to 0.08 μm resulting in liposomes having diameters in the approximate range of 120±10 nm.

Liposomes of the invention are typically prepared with lipid components present in a molar ratio of about 70–90 percent vesicle-forming lipids, 1–20 percent of a polymer-lipid conjugate for forming the surface coating of releasable polymer chains, and 0.1–5 percent of an end-functionalized polymer lipid conjugate for the coupling of targeting moieties. It will be appreciated that the polymer-lipid conjugate with the releasable linkage can be end-functionalized to couple a targeting ligand, or the liposomes can include two different polymer-lipid species—one polymer-lipid conjugate with a releasable linkage and another polymer-lipid conjugate with no releasable linkage but with an attached targeting moiety.

In studies performed in support of the invention, both pH-sensitive and non pH-sensitive liposomes were prepared as described in Example 1. pH-sensitive, sterically stabilized liposomes, either targeting or non-targeting, and having either a releasable or non-releasable coating were prepared from a mixture of DOPE or DOPE/CHEM (6:4 molar ratio), and including either mPEG-DSPE (non-releasable) or mPEG-S-S-DSPE (releasable coating) and, in some cases, a maleimide-terminated polyethyelenglycol coupled to DSPE, Mal-PEG-DSPE, capable of attachment of a targeting ligand. The lipid molar ratios of the different formulations are indicated in the Figure legends and the description for each of the experiments.

Non pH-sensitive liposomes were prepared from hydrogenated soy phosphatidylcholine (HSPC), cholesterol (CHOL), mPEG-DSPE and either maleimide-PEG-DSPE (targeting) or not (non-targeting) having the molar ratios of 2:1:0.08:0.02 HSPC/CHOL/mPEG-DSPE/maleimide-PEG- DSPE or 2:1:0.08 HSPC/CHOL/mPEG-DSPE, respectively. The liposomes were formed by the hydration technique by dissolving the lipid components in chloroform. After mixing the components, chloroform was removed and the dried lipid films were hydrated with an appropriate buffer and sequentially extruded through a series of polycarbonate filters with pore sizes ranging from 0.2 to 0.08 μm.

The therapeutic drug doxorubicin (DXR) was encapsulated into preformed liposomes by remote loading following an ammonium sulfate gradient method, as described in Example 1. In some studies, pH-sensitive liposomes were also loaded with trisodium 8-hydroxypyrenetrisulfonate p-xylene-bis-pyridimium (HPTS-DPX), a fluorescent dye, or with radiolabeled tyraminylinulin ([$^{125}$I]TI) to assess the stability of the liposome bilayer. Encapsulation of HPTS-DPX or [$^{125}$I]TI was accomplished by hydrating the thin lipid film with a solution (pH 9.0) of the desired compound, as described in Example 1.

In some studies, described below, targeted liposomes having an anti-CD19 antibody coupled to maleimide-terminus of the Mal-PEG-DSPE were prepared according to the procedure described in Example 2.

In vitro Stability of the Liposome Composition

The pH-sensitive liposomes herein described are stabilized by a releasable polymer coating, thus allowing the liposomes to retain an encapsulated compound even at acidic pHs. The pH sensitivity of the liposomes, and therefore destabilization at acidic pHs, is restored by cleaving all or a portion of the polymer coating, to cause destabilization of the liposomes and concomitant release of the liposomal contents. This feature of the liposome composition was demonstrated by in vitro leakage experiments, described in Examples 3–5. The stability of the pH-sensitive liposomes was compared to that of non-pH sensitive liposomes in buffers at pH 7.4 or pH 5.5, with or without dithiothreitol (DTT), in cell-free extract (CFE), in human plasma, and in cell-culture medium containing 10% fetal bovine serum (FBS). The release or leakage of entrapped solute, either trisodium 8-hydroxypyrenetrisulfonate-p-xylene-bis-pyridinium bromide (HPTS-DPX, a fluorescent dye), or doxorubicin (DXR), from the liposomes was measured using a fluorescence-dequenching assay.

Stability of pH-sensitive Liposomes in Buffers

Leakage of HPTS from DOPE (FIGS. 4A–4B) and DOPE/CHEMS (FIGS. 5A–5B) liposomes stabilized with mPEG-DSPE (FIGS. 4A and 5A) or mPEG-S-S-DSPE (FIGS. 4B and 5B) and incubated in pH 7.5 and pH 5.5 buffers at 37° C. was evaluated by the procedure described in Example 3. Additionally, the leakage of HPTS from liposomes containing mPEG-S-S-DSPE incubated in pH 7.4 and in pH 5.5 buffers in the presence of dithiothreitol (DTT) (100 nM) was evaluated (FIG. 5B). DTT induces thiolytic cleverage of the disulfide bond and causes release of the stabilizing polymer coating.

Figure 4A:
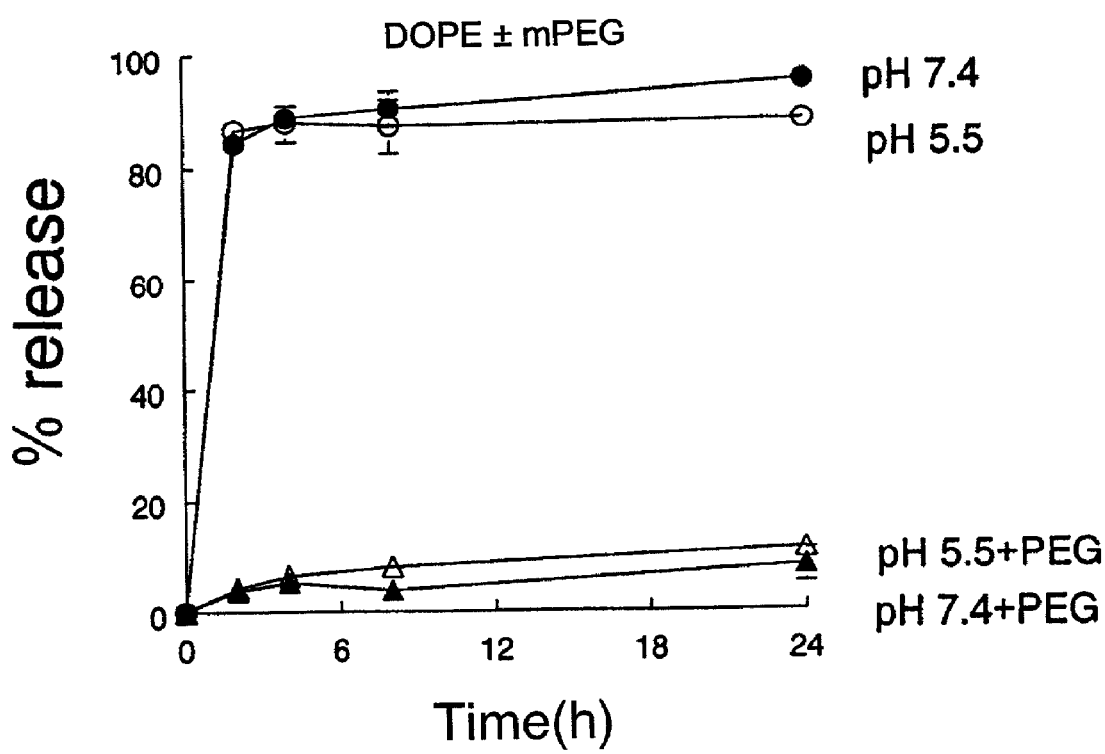
FIGS. 4A–4B illustrate the leakage of encapsulated fluorescent dye as a function of time (hr), determined as the percentage increase in the sample fluorescence over that of the pre-incubation sample treated with Triton X-100 (100% release), from dioleoylphosphatidylethanolmaine (DOPE) liposomes stabilized with various PEG-DSPE conjugates (cleavable or non-cleavable) in buffer at either pH 7.4 or pH 5.5, at 37° C. in the presence or absence of dithiothreitol (DTT); results are from a representative experiment, and are means of triplicate analyses±S.D. (error bars are smaller than markers in many cases); in (A) ●, DOPE, no PEG-DSPE, pH 7.4;○, DOPE, no PEG-DSPE, pH 5.5;▲, DOPE/mPEG-DSPE, pH 7.4;Δ, DOPE/mPEG-DSPE, pH 5.5, in (B) ■, DOPE/mPEG-S-S-DSPE, pH 7.4;▼, DOPE/mPEG-S-S-DSPE, pH 5.5;□, DOPE/mPEG-S-S-DSPE+DTT, pH 7.4;∇, DOPE/mPEG-S-S-DSPE+DTT, pH 5.5.
Figure 4B:
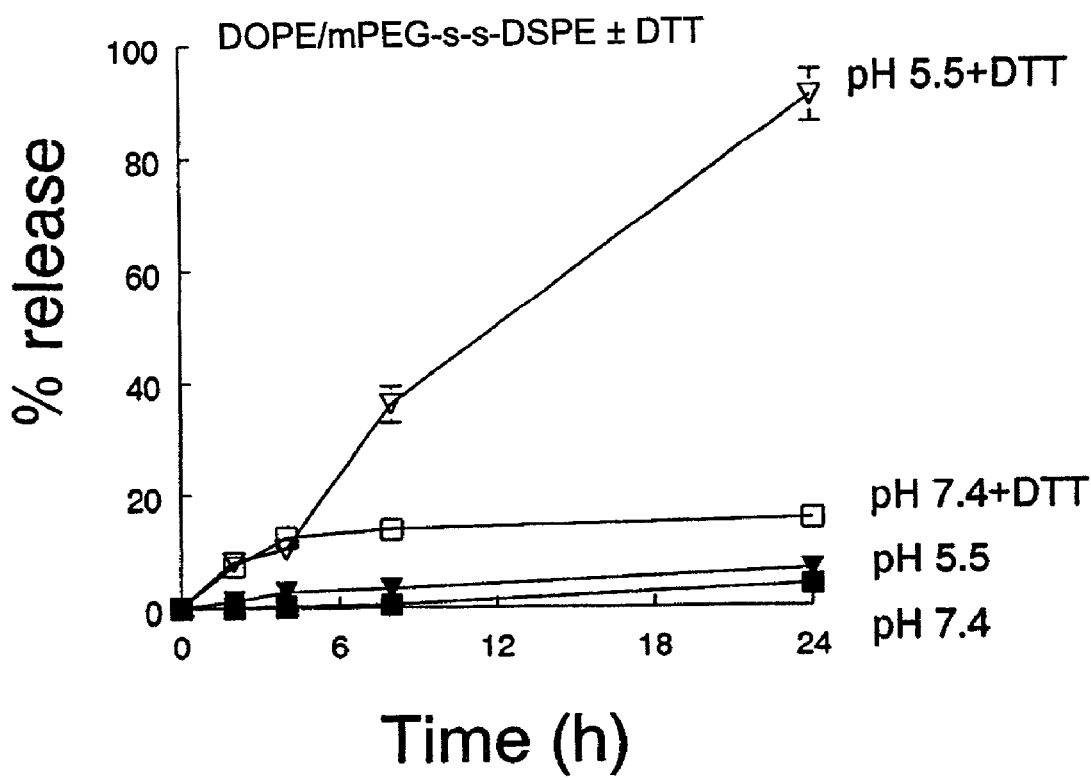

As shown in FIGS. 4A and 4B, pH sensitive liposomes can be stabilized in a bilayer state by the inclusion of a small molar percentage of a molecule having a bulky headgroup. That is, a PEG-lipid derivative can stabilize DOPE or DOPE/CHEMS in the bilayer state in the pH range of 5.5–7.4, and the pH sensitivity of the liposome is restored when the coating is released. Liposomes formed from DOPE only release their contents when incubated in pH 7.4 buffer (●) or in pH 5.5 buffer (○) (FIG. 4A). Incorporation of 5 mol % mPEG-DSPE (FIG. 4A) or mPEG-S-S-DSPE (FIG. 4B) into the DOPE formulation resulted in the formation of liposomes which did not leak when incubated in pH 7.4 buffer (▲, 5 mol % of mPEG-DSPE (FIG. 4A), and ■, 5 mol % of mPEG-S-S-DSPE (FIG. 4B)) or in pH 5.5 buffer (Δ, 5 mol % of mPEG-DSPE (FIG. 4A), and ▼, 5 mol % of mPEG-S-S-DSPE (FIG. 4B) over 24 hours.

Treatment of liposomes with dithiothreitol (DTT) induce thiolytic cleavage of mPEG-S-S-DSPE from the lipid membrane anchor (DSPE). DOPE liposomes containing 5 mol % mPEG-S-S-DSPE had little contents release over 24 hours in the presence of DTT at pH 7.4 (■, FIG. 4B); however at pH 5.5, treatment with DTT led to a gradual release of HPTS of approximately 50% in about 10 h (▼, FIG. 4B). At pH 5.5, a DOPE formulation that contained 3 mol % mPEG-S-S-DSPE had a much more rapid release of contents (100% release in 2 h, data not shown).

Figure 5A:
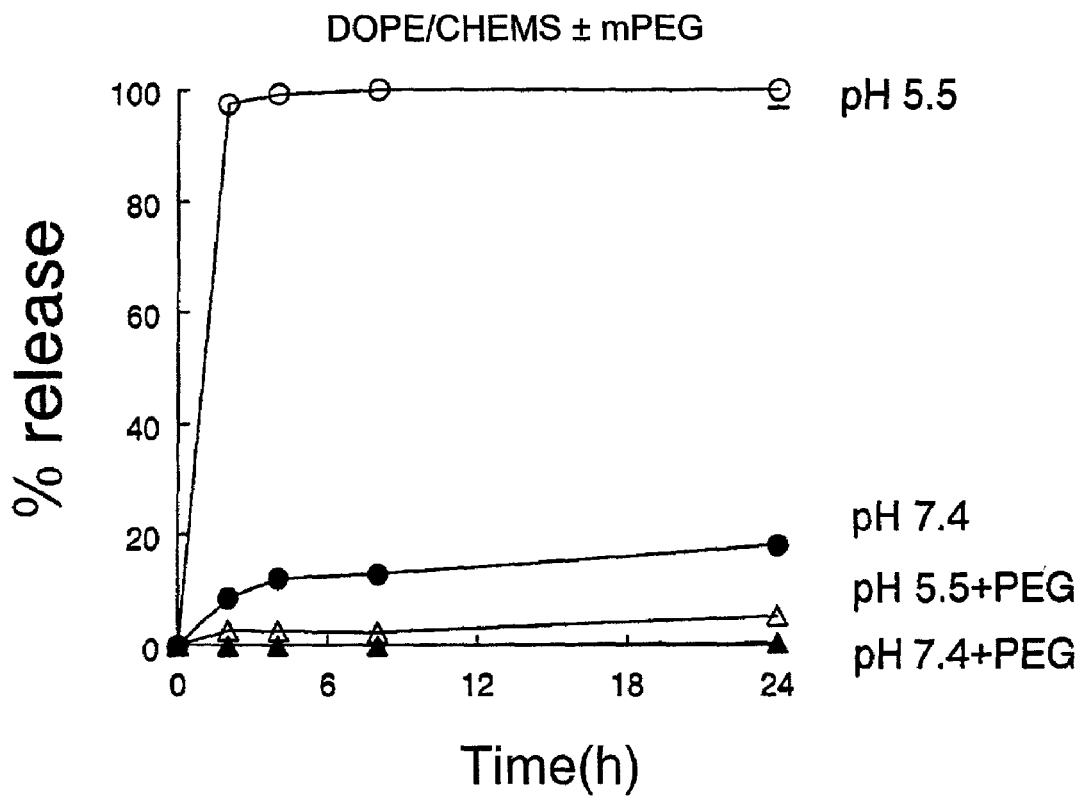
FIGS. 5A–5B illustrate the leakage of encapsulated fluorescent dye as a function of time (hr), determined as the percentage increase in the sample fluorescence over that of the pre-incubation sample treated with Triton X-100 (100% release), from DOPE/CHEMS liposomes stabilized with 5 mol % mPEG-DSPE or 5 mol % mPEG-S-S-DSPE conjugates (cleavable or non-cleavable) in buffer at either pH 7.4 or pH 5.5, at 37° C. in the presence or absence of dithiothreitol (DTT); results are from a representative experiment, and are means of triplicate analyses±S.D. (error bars are smaller than markers in many cases); in (A) ●, DOPE/CHEMS only, pH 7.4; ○, DOPE/CHEMS only, pH 5.5;▲, DOPE/CHEMS/mPEG-DSPE, pH 7.4;Δ, DOPE/CHEMS/mPEG-DSPE, pH 5.5; in (B) ■, DOPE/CHEMS/mPEG-S-S-DSPE, pH 7.4;▼, DOPE/CHEMS/mPEG-S-S-DSPE, pH 5.5;□, DOPE/CHEMS/mPEG-S-S-DSPE+DTT, pH 7.4; ∇, DOPE/CHEMS/mPEG-S-S-DSPE+DTT, pH 5.5.
Figure 5B:
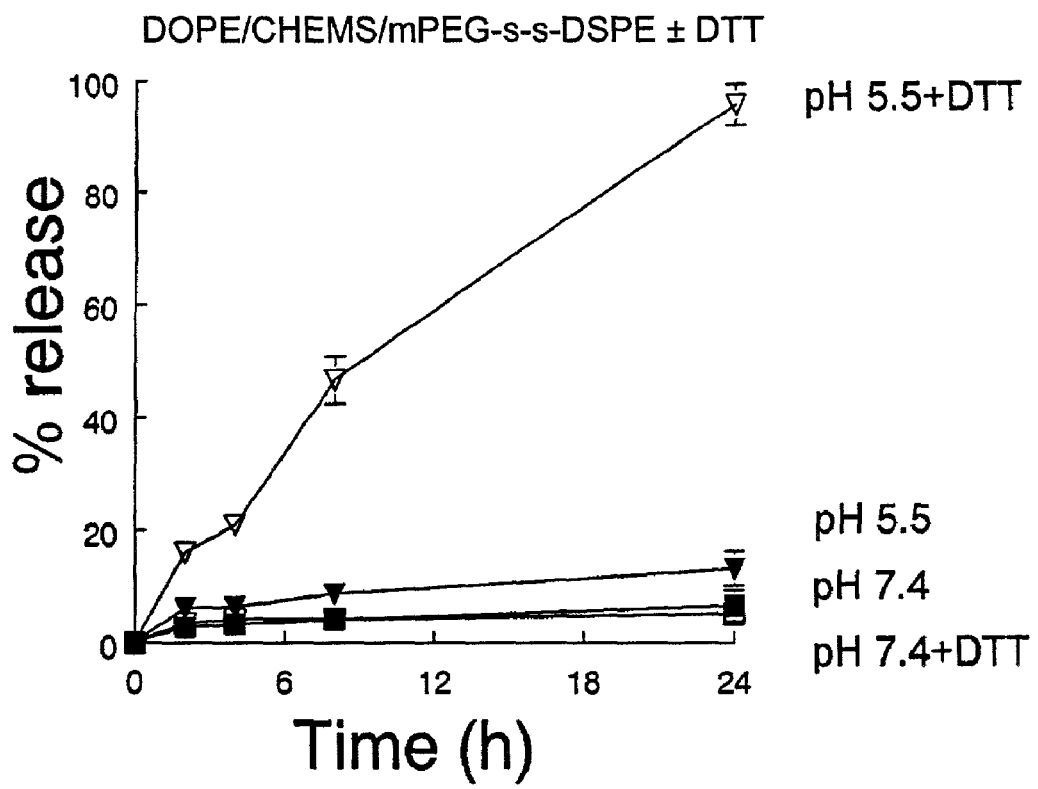

As illustrated in FIGS. 5A and 5B, DOPE liposomes can also be stabilized in the bilayer state by an amphiphile with bulky and/or charge-repulsing hydrophilic moieties. DOPE/CHEMS formulations without mPEG-DSPE had little leakage at pH 7.4 (●, FIG. 5A), but rapidly released the encapsulated dye at pH 5.5 (○, FIG. 5A). At pH 5.5 or 7.4, less than 10% leakage occurred over 24 hours when these liposomes were stabilized with either 5 mol % mPEG-DSPE (FIG. 5A: Δ, at pH 5.5 and ▲, at pH 7.4), or 5 mol % of mPEG-S-S-DSPE (FIG. 5B: ▼, at pH 5.5 and ■, at pH 7.4). In the presence of DTT, DOPE/CHEMS liposomes containing 5 mol % mPEG-S-S-DSPE had a release half-life of approximately 8 hours at pH 5.5 (∇, FIG. 5B) while little release occurred at pH 7.4 (□, FIG. 5B). DTT treatment of DOPE/CHEMS liposomes stabilized with 3 mol % mPEG-S-S-DSPE resulted in intermediate leakage rates (data not shown).

As seen in FIGS. 4B and 5B, pH-sensitive liposomes containing mPEG-S-S-DSPE (▼, in both FIGS. 4B and 5B) have an increased rate of contents release at pH 5.5, although contents release is less rapid than that seen for similar liposomes lacking PEG (○, FIGS. 4A and 5A). This less rapid release may be due in part to an incomplete cleavage of mPEG-S-S-DSPE, a feature that can advantageously utilized to vary and tailor the release rate of an entrapped agent. For example, selection of a releasable bond which fails to undergo complete release can be used to slow the content release rate, whereas selection of a bond that readily cleaves in response to the selected stimulus can be used to achieve total, rapid release of the entrapped agent.

Stability of pH Sensitive Liposomes in Cell-free Extract (CFE)

Cell free extract (CFE) contains cytoplasmic and lysosomal enzymes capable of mimicking the action of dithiothreitol (DTT) in cleaving mPEG-S-S-DSPE. The leakage of the hydrophilic, membrane-impermeable dye trisodium 8-hydroxypyrenetrisulfonate (HPTS) from formulations exposed to CFE is therefore indicative of the process of destabilization in an intracellular environment of pH-sensitive liposomes stabilized with either mPEG-DSPE or mPEG-S-S-DSPE.

Figure 6A:
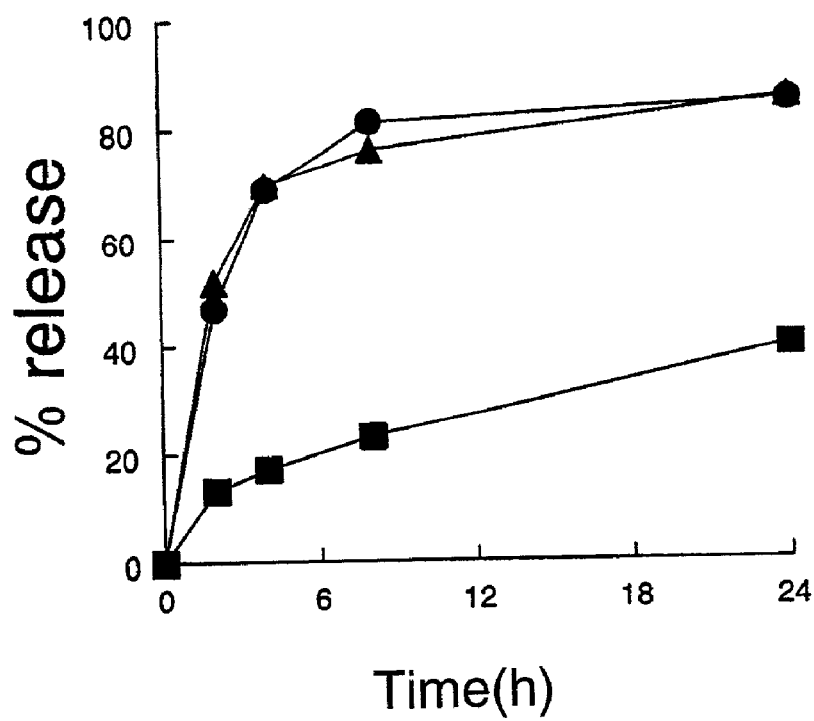
FIGS. 6A–6B illustrates the leakage of encapsulated fluorescent dye as a function of time (hr), from DOPE liposomes (A) or DOPE/CHEMS liposomes (B) either not stabilized or stabilized with different proportions of mPEG-S-S-DSPE in the lipid mix, incubated in cell-free extract adjusted to pH 5.5 at 37° C.; the leakage is determined as the percentage increase in the sample fluorescence over that of the pre-incubation sample treated with Triton X-100 (100% release); results are from a representative experiment, and are means of triplicate analyses±S.D.; in (A) ●, DOPE alone; ▲, DOPE/mPEG-S-S-DSPE (1:0.03); ■, DOPE/mPEG-S-S-DSPE (1:0.05); in (B) ○, DOPE/CHEMS (6:4); Δ, DOPE/CHEMS/mPEG-S-S-DSPE (6:4:0.18); □, DOPE/CHEMS/mPEG-S-S-DSPE (6:4:0.3).
Figure 6B:
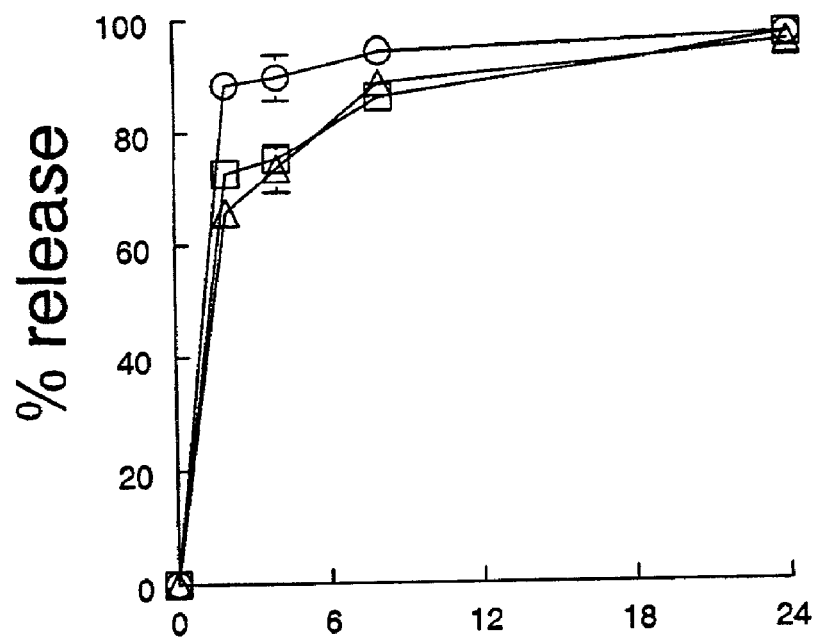

FIGS. 6A–6B show the leakage of encapsulated HPTS dye as a function of time from DOPE or DOPE/CHEMS liposomes stabilized with different proportions of mPEG-S-S-DSPE in the lipid mix, incubated in cell-free extract adjusted to pH 5.5 (approximately the lysosomal pH of between 5 and 6.5) at 37° C. The study was performed according to the procedure described in Example 4. The leakage was determined as the percentage increase in the sample fluorescence over that of the pre-incubation sample treated with Triton X-100 (100% release); results are from a representative experiment, and are means of triplicate analyses±S.D.

FIG. 6A shows the percent release of HPTS dye as a function of time for liposomes consisting of DOPE (●), of DOPE stabilized with 3 mol % mPEG-S-S-DSPE (▲) and with 5 mol % mPEG-S-S-DSPE (■). The liposomes made of DOPE alone or DOPE stabilized with 3 mol % mPEG-S-S-DSPE underwent a rapid release of their contents, with half-lives of 1.7 hour. The release rate in CFE of the DOPE formulation with 5 mol % mPEG-S-S-DSPE (■) was slower with 40% of encapsulated dye released over 24 hours.

FIG. 6B shows the percent release of HPTS entrapped in liposomes made of DOPE/CHEMS (○), DOPE/CHEMS/1.8 mol % mPEG-S-S-DSPE (Δ); and DOPE/CHEMS/3 mol % mPEG-S-S-DSPE (□). The three formulations had a rapid release of their contents in the CFE at pH 5.5, with a near complete release by 8 hours. DOPE/CHEMS and DOPE/CHEMS/mPEG-S-S-DSPE formulations incubated in CFE adjusted to pH 7.4 released HPTS at much slower rates (data not shown).

pH-sensitive Liposome Stability in Human Plasma

In another study, detailed in Example 5, the leakage rates of hydrophilic dye from various liposome formulations were evaluated in 90% human plasma (pH 7.4) at 37° C. and in cell culture media containing 10% FBS at 37° C. HPTS was passively loaded into liposomes as the water-soluble (but fluorescence-quenched) complex, HPTS-DPX. When HPTS-DPX leaks from the liposomes, it dissociates into free HPTS and DPX, increasing the HPTS fluorescence when excited at 413 nm. It was found that less than 20% of encapsulated HPTS leaked from DOPE/mPEG-DSPE, DOPE/CHEMS/mPEG-DSPE, DOPE/mPEG-S-S-DSPE or DOPE/CHEMS/mPEG-S-S-DSPE formulations over 24 hours in human plasma (not shown).

Figure 7A:
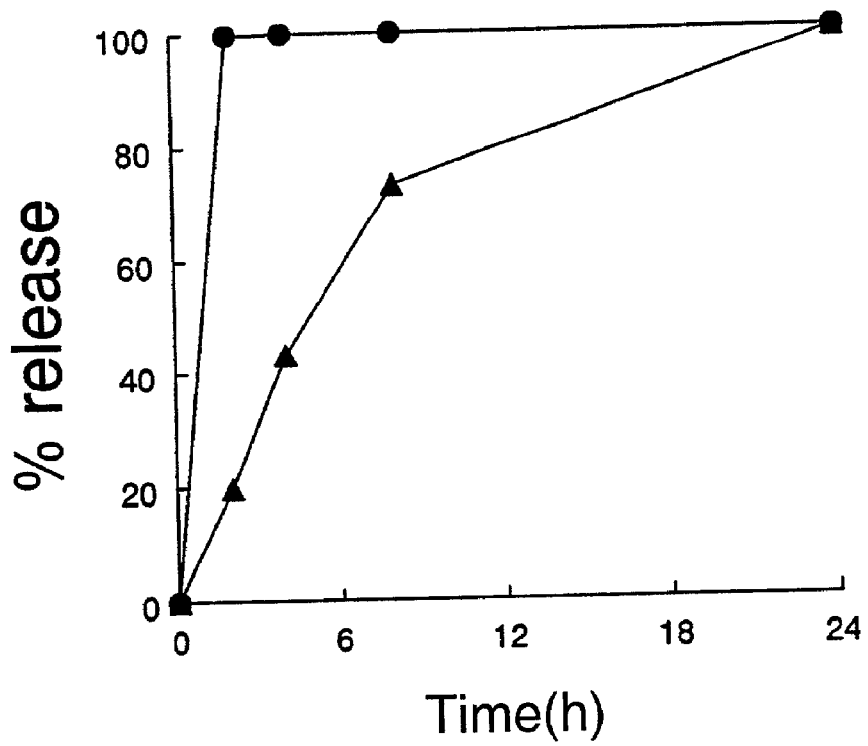
FIGS. 7A–7B illustrate the leakage as a function of time (hr), after incubation in human plasma (pH 7.4) at 37° C., of encapsulated doxorubicin from DOPE or DOPE/CHEMS liposomes containing anti-CD19 as a targeting moiety and either mPEG-DSPE or mPEG-S-S-DSPE; the released DXR was determined as the percentage increase in the sample fluorescence over that of samples preincubated with Triton X-100; the results are from a representative experiment, and are means of triplicate analyses±S.D.; (A) ●, anti-CD19-targeted, DXR-loaded DOPE/mPEG-DSPE/Mal-PEG-DSPE (1:0.04:0.01); ▲, anti-CD19-targeted, DXR-loaded DOPE/CHEMS/mPEG-DSPE/Mal-PEG-DSPE (6:4:0.2:0.1); (B) ■, anti-CD19-targeted, DXR-loaded DOPE/mPEG-S-S-DSPE/Mal-PEG-DSPE (1:0.04:0.01); ▼, anti-CD19-targeted, DXR-loaded DOPE/CHEMS/mPEG-S-S-DSPE/Mal-PEG-DSPE (6:4:0.2:0.1).
Figure 7B:
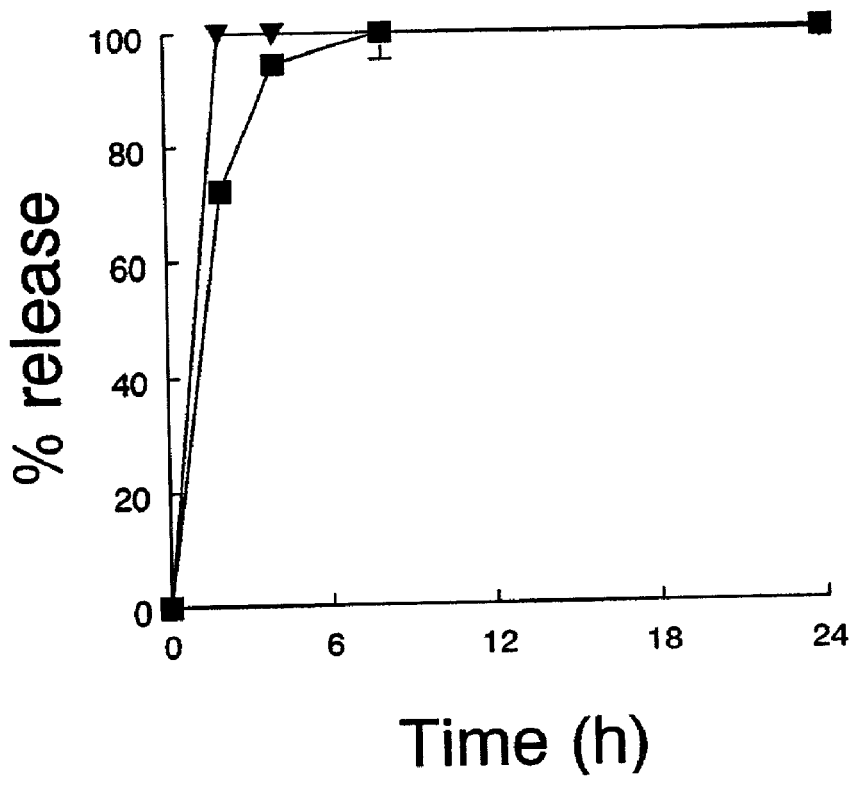

Doxorubicin (DXR) is normally actively loaded into liposomes at a pH of about 5.5, using an ammonium sulfate gradient to form a precipitate ((DXR-NH$_3$)$_2$SO$_4$) inside the liposomes (Bolotin et al., *J. Liposome Res.*, 4:455 (1994)). This liposomal doxorubicin formulation is very stable with a slow rate of drug release. However, at the higher pH required to assemble DOPE or DOPE/CHEMS lipids into liposomes, it was not heretofore known whether DXR forms a precipitate inside the liposomes during active loading, and what the release rate of DXR from pH-sensitive liposomes would be. As seen in FIGS. 7A–7B, the leakage of DXR in human plasma was examined for anti-CD 19-targeted pH-sensitive liposomes comprised of DOPE/4 mol % mPEG-DSPE, (●); DOPE/CHEMS/2 mol % mPEG-DSPE (▲), DOPE/4 mol % mPEG-S-S-DSPE (■) and DOPE/CHEMS/2 mol % mPEG-S-S-DSPE (▼). DXR was rapidly released from all of the formulations, with the exception of DOPE/CHEMS/mPEG-DSPE (▲, FIG. 7A) which had a somewhat slower, but still rapid, release rate. There was no significant difference in the rate of DXR release between the anti-CD 19-targeted and similar non-targeted formulations (containing 5 mol % mPEG) in the presence of human plasma (data not shown).

The stability of various pH-sensitive liposome compositions in cell culture media containing 10% FBS was also evaluated. All of the liposomes tested includes an anti-CD19 targeting ligand and contained DXR entrapped in the interior compartments. The liposome lipid compositions were comprised of DOPE/4 mol % mPEG-DSPE, DOPE/CHEMS/2 mol % mPEG-DSPE, DOPE/4 mol % mPEG-S-S-DSPE and DOPE/CHEMS/2 mol % mPEG-S-S-DSPE. All of the liposome compositions were stable in that there was less than 10% DXR leakage over 24 hours of incubation at 37° C. (data not shown).

Drug Delivery Efficacy of the Liposomal Composition

In accord with the method of the invention, the liposomes described above are capable of releasing their contents rapidly in response to lower pH conditions in or just outside of a target cell, to achieve an increased intracellular concentration of the drug, when compared to non-pH sensitive, targeted liposomes or to non-pH sensitive, non-targeted liposomes. This increased intracellular concentration was demonstrated in studies performed to support the invention described in Part A below. In these studies, the rate of accumulation of doxorubicin in cell nuclei was determined, since the rate of release of liposome-encapsulated doxorubicin from the lysosomal apparatus to the cell nuclei following internalization of targeted liposomes is a determining factor for the cytotoxicity of liposome-encapsulated doxorubicin. The results of the doxorubicin nuclear accumulation assay are discussed in Part B. Part C describes studies of the blood elimination of the liposomes in a mouse model, and Part D illustrates, with in vivo studies, the improved therapeutic effect achievable by the treatment method of the invention.

In Vitro Cytotoxicity of Targeted, Stabilized, pH-sensitive Liposomes

In vitro cytotoxicity of free DXR and various liposomal formulations was evaluated using Namalwa cells with an in vitro proliferation assay as described in Example 6. The liposome formulations evaluated are listed in Table 1. In addition to the targeted, pH-sensitive liposomes, conventional, non-pH sensitive sterically stabilized liposome (DXR-SL) and doxorubicin in free form were also tested. Each of the test formulations was incubated with the Namalwa cells under controlled conditions for 48 hours. At the end of the incubation time, cytotoxicity was expressed as the inhibitory concentration, that is the concentration required for a 50% inhibition of cell growth (IC$_{50}$). The results are shown in Table 1.

TABLE 1

Cytotoxicity of free doxorubicin (DXR) and liposomal formulations of DXR (with or without anti-CD 19) to CD19+ Namalwa cells

| Formulation of DXR-loaded liposomes | IC$_{50}$ (μM DXR)[1] |
|---|---|
| DOPE/mPEG-DSPE (1:0.05) | 7.0 ± 2.2 |
| DOPE/mPEG-DSPE/Mal-PEG-DSPE[anti-CD 19] (1:0.04:0.01) | 0.2 ± 0.1 |
| DOPE/mPEG-S-S-DSPE (1:0.03) | 8.9 ± 4.7 |
| DOPE/mPEG-S-S-DSPE/Mal-PEG-DSPE[anti-CD19] (1:0.02:0.01) | 1.5 ± 0.7 |
| DOPE/CHEMS/mPEG-DSPE (6:4:0.3) | 4.2 ± 1.1 |
| DOPE/CHEMS/mPEG-DSPE/Mal-PEG-DSPE [anti-CD19] (6:4:0.24:0.06) | 0.4 ± 0.1 |
| DOPE/CHEMS/mPEG-S-S-DSPE (6:4:0.18) | 6.0 ± 0.8 |
| DOPE/CHEMS/mPEG-S-S-DSPE/Mal-PEG-DSPE [anti-CD19] (6:4:0.12:0.06) | 3.3 ± 1.0 |
| HSPC/CHOL/mPEG-DSPE ("DXR-SL") | >200 |
| HSPC/CHOL/mPEG-DSPE/Mal-PEG-DSPE[anti-CD19] (2:1:0.08:0.02) ("DXR-SIL") | 35.4 ± 12.7 |
| Free DXR | 0.8 ± 0.7 |

[1]Cytotoxicities were determined by the MTT assay and are expressed as mean drug concentration at which cell growth was inhibited by 50% (IC$_{50}$ ± SD).

As shown in Table 1, all the DOPE or DOPE/CHEMS formulations, either targeted or non-targeted, had significantly lower IC$_{50}$s than the DXR-SL (HSPC/CHOL/mPEG- DSPE) or DXR-SIL[anti-CD 19] (HSPC/CHOL/mPEG-DSPE/Mal-PEG-DSPE[anti-CD 19]) formulations (P<0.001). The significantly lower $IC_{50}$s is likely due to the rapid release rate of doxorubicin from the DOPE or DOPE/CHEMS formulations compared to the release of doxorubicin from DXR-SL or DXR-SIL[anti-CD19], which have a considerably slower release rate of drug (Lopes de Menezes et al., Cancer Res., 58:3320 (1998)). Targeted DOPE and DOPE/CHEMS formulations had $IC_{50}$s that were comparable in most instances to those for free doxorubicin (Table 1). The $IC_{50}$s of doxorubicin-loaded targeted formulations of either DOPE or DOPE/CHEMS (stabilized with mPEG-DSPE or mPEG-S-S-DSPE) were significantly lower than the $IC_{50}$s of the non-targeted formulations (P<0.05 to P<0.001). Notably, there was a trend for formulations that contained mPEG-DSPE to be slightly more cytotoxic than those that contained mPEG-SS-DSPE, whether targeted or non-targeted. Targeted formulations without encapsulated doxorubicin were not toxic at concentrations below 0.06 μM DOPE, which would correspond to a doxorubicin concentration of 34.5 μM, if the formulations contained doxorubicin (not shown).

It is clear from the data in Table 1 that pH-sensitive liposomes, targeted or not targeted, have a significantly lower $IC_{50}$ than non-pH sensitive liposomes (e.g., the liposomes prepared from HSPC/CHOL/mPEG-DSPE). The $IC_{50}$ of non-pH sensitive liposomes was 200 μM doxorubicin and 35 μM doxorubicin for non-targeted and targeted formulations, respectively. Use of pH-sensitive lipids DOPE or DOPE/CHEMS rather than HPSC/CHOL resulted in between a 22–48 fold decrease in $IC_{50}$. This substantial increase in cytotoxicity was unexpected, and accordingly the invention contemplates a method for increasing the cytotoxicity of a liposome-entrapped drug by at least about 10-fold, more preferably by about 20-fold, and most preferably by about 40-fold, by entrapping the drug in a pH-sensitive liposome. Also seen from the data in Table 1 is the increased cytotoxicity achieved by including a targeting ligand to the pH-sensitive liposomes. The invention thus contemplates increasing the cytotoxicity of a drug entrapped in a pH-sensitive liposome by including a targeting ligand on the liposome. The targeting ligand is effective to achieve at least a 2-fold, preferably a 4-fold, more preferably a 6-fold, and most preferably a 10-fold increase in cytotoxicity, as measured by a decrease in $IC_{50}$ relative to pH-sensitive liposomes lacking the targeting ligand.

Nuclear Accumulation Assay

Nuclear accumulation of doxorubicin was determined as described in Example 7. Briefly, Namalwa cells, maintained under logarithmic growth conditions were treated with doxorubicin-entrapped liposome formulations at a doxorubicin concentration of 8 μM. At various time points (0, 2, 4, 8, 12 hours), an aliquot of the treated cells was ruptured to recover the nuclei. The DNA in the nuclei were enzymatically digested and doxorubicin fluorescence was measured. The results are shown in FIGS. 8A–8C.

Figure 8A:
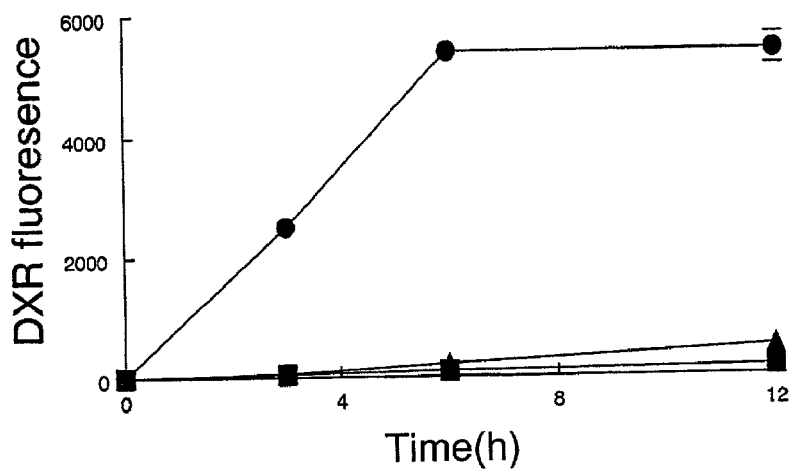
FIGS. 8A–8C illustrate in vitro nuclear accumulation of doxorubicin in Namalwa cells with time, after treatment with doxorubicin encapsulated in liposomes; results are from a representative experiment, and are means of triplicate analyses±S.D.; in (A) ●, free doxorubicin; ■, doxorubicin-containing liposomes of HSPC/CHOL/mPEG-DSPE, 2:1:0.1;▲, anti-CD19 targeted doxorubicin-containing liposomes of HSPC/CHOL/mPEG-DSPE/Mal-PEG-DSPE, 2:1:0.08:0.02; in (B) ●, anti-CD19-targeted doxorubicin-containing liposomes of DOPE/mPEGDSPE/Mal-PEG-DSPE, 1:0.04:0.01;▲, anti-CD19 targeted doxorubicin-containing liposomes of DOPE/CHEMS/mPEG-DSPE/Mal-PEG-DSPE, 6:4:0.24:0.06;○, doxorubicin-containing liposomes of DOPE/mPEG-DSPE, 1:0.05; 0, DXR-DOPE/CHEMS/mPEG-DSPE, 6:4:0.3; in (C) ▼, anti-CD19 targeted doxorubicin-containing liposomes of DOPE/CHEMS/mPEG-S-S-DSPE/Mal-PEG-DSPE, 6:4:0.12:0.06; ■, anti-CD19targeted doxorubicin-containing liposomes of DOPE/mPEG-S-S-DSPE/Mal-PEG-DSPE, 1:0.02:0.01;□, non-targeted doxorubicin-containing liposomes of DOPE/mPEG-S-S-DSPE, 1:0.03;∇, non-targeted doxorubicin-containing liposomes of DOPE/CHEMS/mPEG-S-S-DSPE, 6:4:0.18.

FIG. 8A compares the nuclear accumulation of doxorubicin, as measured by doxorubicin fluoresence, in Namalwa cells treated with free doxorubicin (●); doxorubicin-encapsulated, non-targeted, non-pH sensitive liposomes (■) (HSPC/CHOL/mPEG-DSPE, 2:1:0.1 molar ratio); and doxorubicin encapsulated, targeted, non-pH sensitive liposomes (▲) (HSPC/CHOL/mPEG-DSPE/Mal-PEG-DSPE, 2:1:0.08:0.02 molar ratio). As seen, little measurable doxorubicin is found in the nuclei after administration from non-pH sensitive liposomes.

Figure 8B:
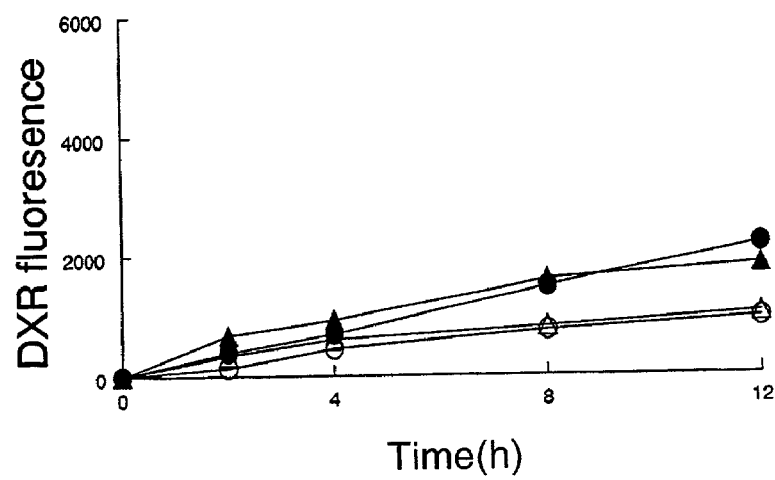

FIG. 8B compares the nuclear accumulation of doxorubicin in Namalwa cells treated with doxorubicin encapsulated anti-CD19-targeted liposomes composed of DOPE/mPEGDSPE/Mal-PEG-DSPE, 1:0.04:0.01 molar ratio (●); doxorubicin encapsulated anti-CD19-targeted liposomes composed of DOPE/CHEMS/mPEG-DSPE/Mal-PEG-DSPE, 6:4:0.24:0.06 molar ratio (▲); doxorubicin-encapsulated liposomes composed of DOPE/mPEG-DSPE, 1:0.05 molar ratio (○); doxorubicin-encapsulated liposomes composed of DOPE/CHEMS/mPEG-DSPE, 6:4:0.3 molar ratio (Δ). As seen, the pH-sensitive liposomes result in accumulation of the drug in the nucleus (compared with non-pH sensitive liposomes shown in FIG. 8A), with addition of a targeting ligand effective to achieve a higher level of accumulation.

Figure 8C:
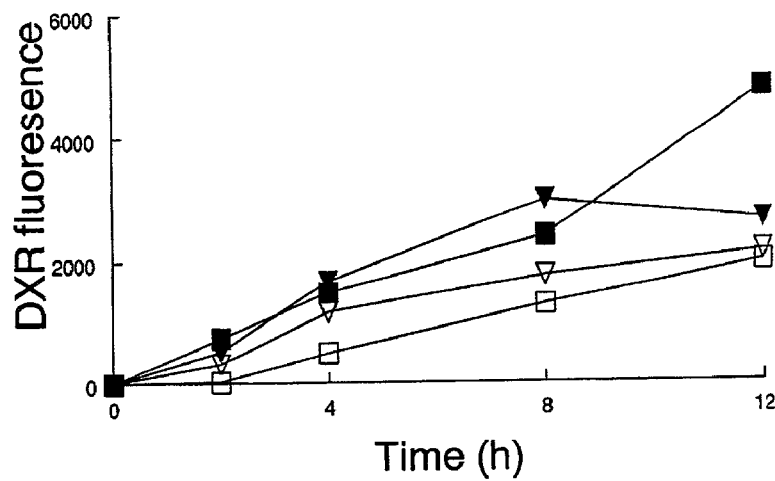

FIG. 8C shows the nuclear accumulation of doxorubicin in Namalwa cells treated with doxorubicin encapsulated, anti-CD19-targeted liposomes composed of DOPE/CHEMS/mPEG-S-S-DSPE/Mal-PEG-DSPE, 6:4:0.12:0.06 molar ratio (▼); anti-CD19-targeted liposome composed of DOPE/mPEG-S-S-DSEP/Mal-PEG-DSPE, 1:0.02:0.01 molar ratio (■); non-targeted liposome composed of DOPE/mPEG-S-S-DSPE, 1:0.03 molar ratio (□); non-targeted liposomes composed of DOPE/CHEMS/mPEG-S-S-DSPE, 6:4:0.18 molar ratio (∇). As seen, pH-sensitive liposomes with releasable PEG chains and a targeting ligand achieve accumulation of the liposome entrapped drug in the cell nucleus.

The data presented in FIGS. 8A–8C show that free doxorubicin accumulated within the nuclei at the fastest rate (FIG. 8A). Rates of doxorubicin release for targeted mPEG-DSPE-stabilized (FIG. 8B) or mPEG-S-S-DSPE-stabilized (FIG. 8C) DOPE or DOPE/CHEMS formulations were much faster than that of targeted non-pH sensitive liposomes (FIG. 8A). The order of nuclear accumulation of doxorubicin from liposomal formulations was: free drug>targeted, pH-sensitive mPEG-S-S-DSPE>targeted pH-sensitive mPEG-DSPE>non-targeted pH-sensitive mPEG-S-S-DSPE>non-targeted, pH-sensitive mPEG-DSPE>targeted non-pH sensitive>non-pH sensitive. Interestingly, although not more cytotoxic than mPEG-containing formulations (Table 1), formulations containing mPEG-S-S-DSPE appeared to result in more rapid nuclear accumulations of doxorubicin over the time course of these experiments.

The cytotoxicity ($IC_{50}$) values reported in Table 1 parallel the nuclear accumulation data, indicating that the total amount of uptake of liposomal drug as well as the rate of release of the encapsulated drug govern the cytotoxicities of liposomal drugs. Total cellular uptake of liposomal drug can be increased via the mechanism of receptor-mediated internalization, and intracellular drug release can be increased through mechanisms such as the pH-sensitive triggered-release mechanism, described here. Thus, the data supports a method of increasing accumulation of a therapeutic agent into cellular nuclei by providing liposomes described herein, that are comprised of a pH-sensitive lipid, a coating of a releasable polymer chain, and a targeting moiety and administering the liposomes. The administering is effective to achieve (i) cleavage of the releasable bond, to release all or a portion of the hydrophilic polymer chains; (ii), binding between the liposome-bound ligand and the target cell, where the binding can occur prior to or subsequent to the cleavage of the polymer chains; and (iii) internalization of the liposome into the target cell. Internalization of the liposomes will cause exposure of the pH-sensitive lipid to conditions effective to cause destabilization of the liposome, releasing the entrapped contents intracellularly. The administering effectively achieves at least a 2-fold higher accumulation of the liposome-entrapped agent in the cell nucleus that that achieved by liposomes lacking the pH-sensitive lipid, the releasable bond, and/or the targeting ligand.

Blood Pharmacokinetics

The pharmacokinetics of the liposome preparations in mice were evaluated with liposome prepared in accord with the invention and containing radiolabeled [$^{125}$I]TI. As described in Example 8, mice were injected i.v. via the tail vein with a single does of 0.2 ml of [$^{125}$I]TI encapsulated in various liposomal formulations (0.5 μmol PL/mouse). At selected times post-injection blood samples were taken and analyzed for $^{125}$I label. The clearance/elimination of the liposomes from the blood was measured by the decrease of the radioactivity. The results are shown in FIGS. 9A–9D.

Figure 9A:
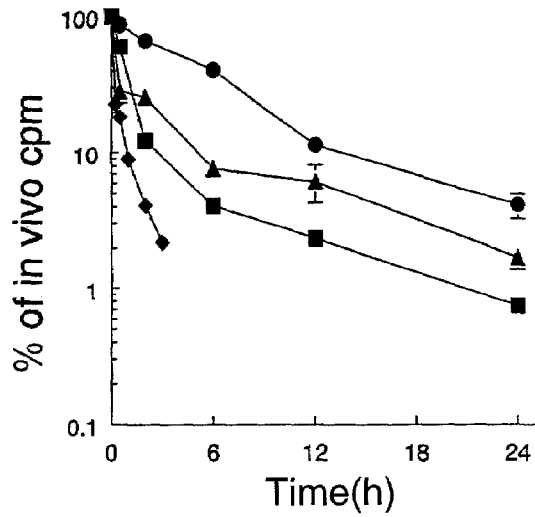
FIGS. 9A–9D illustrate the pharmacokinetics of DOPE or DOPE/CHEMS liposomes in BALB/c mice as measured by the uptake of [$^{125}$I]TI encapsulated in various liposomal formulations (0.5 μmol PL/mouse); results are from a representative experiment, and are means of triplicate analyses±S.D.; in (A) ◊, DOPE; ■, DOPE/mPEG-DSPE, 1.0:0.03;▲, DOPE/mPEG-DSPE, 1.0:0.05;●, DOPE/mPEG-DSPE, 1.0:0.1; in (B) ◊, DOPE/CHEMS; □, DOPE/CHEMS/mPEG-DSPE, 6:4:0.18;Δ, DOPE/CHEMS/mPEG-DSPE, 6:4:0.3;○, DOPE/CHEMS/mPEG-DSPE, 6:4:0.6; in (C) ■, DOPE/mPEG-S-S-DSPE/mPEG-DSPE, 1.0:0.02:0.01;▲, DOPE/mPEG-S-S-DSPE/mPEG-DSPE, 1.0:0.04:0.01;●, DOPE/mPEG-S-S-DSPE/mPEG-DSPE, 1.0:0.09:0.01;(D) ☐, DOPE/CHEMS/mPEG-S-S-/mPEG-DSPE, 6:4:0.012:0.06;△, DOPE/CHEMS/mPEG-S-S-DSPE/mPEG-DSPE, 6:4:0.024:0.06;○, DOPE/CHEMS/mPEG-S-S-DSPE/mPEG-DSPE, 6:4:0.054:0.06.

FIG. 9A shows the elimination of DOPE liposomes, expressed as the percentage of in vivo counts per minute (cpm) as a function of time, in hours, for four liposome compositions having varying content of mPEG-DSPE. The liposome compositions were: DOPE only (♦); DOPE/mPEG-DSPE, 1.0:0.03 molar ratio (■); DOPE/mPEG-DSPE, 1.0:0.05 molar ratio (▲); DOPE/mPEG-DSPE, 1.0:0.1 molar ratio (●). The blood elimination profile varies as the amount of mPEG-DSPE in the liposome varies, with a higher mPEG-DSPE content resulting in a slowing of liposome elimination from the bloodstream.

Figure 9B:
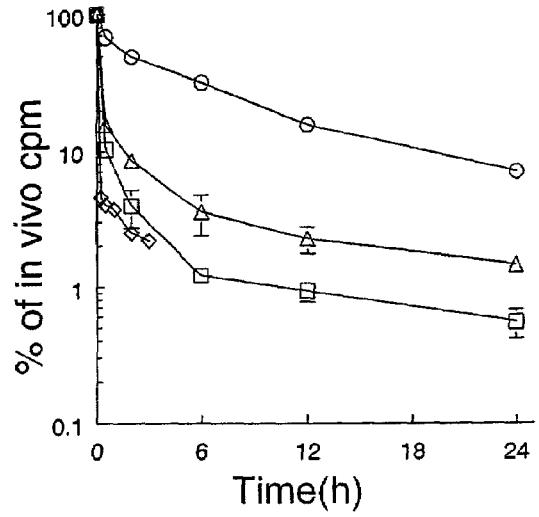

FIG. 9B is a similar plot for liposomes prepared from DOPE/CHEMS and having a varying content of mPEG-DSPE. The liposome formulations were: DOPE/CHEMS, 6:4 molar ratio (□); DOPE/CHEMS/mPEG/DSPE, 6:4:0.18 molar ratio (◊); DOPE/CHEMS/mPEG-DSPE, 6:4:0.3 molar ratio (Δ); DOPE/CHEMS/mPEG-DSPE, 6:4:0.6 molar ratio (○). The blood elimination profile varies as the amount of mPEG-DSPE in the liposome varies, with a higher mPEG-DSPE content resulting in a slowing of liposome elimination from the bloodstream.

Figure 9C:
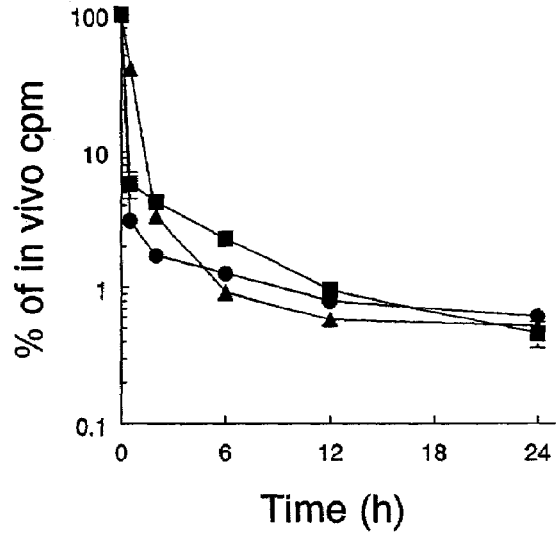

FIG. 9C shows the elimination profile for DOPE liposomes having varying content of mPEG-S-S-DSPE as a function of time. Liposomes composed of DOPE/mPEG-S-S-DSPE/mPEG-DSPE, 1.0:0.02:0.01 molar ratio (■); DOPE/mPEG-S-S-DSPE/mPEG-DSPE, 1.0:0.04:0.01 molar ratio (▲); DOPE/mPEG-S-S-DSPE/mPEG-DSPE, 1.0:0.09:0.01 molar ratio (●) were administered to mice as described in Example 8. Here, there is less dependence on circulation lifetime with increasing amount of mPEG-S-S-DSPE, with the formulations having essentially the same elimination profile.

Figure 9D:
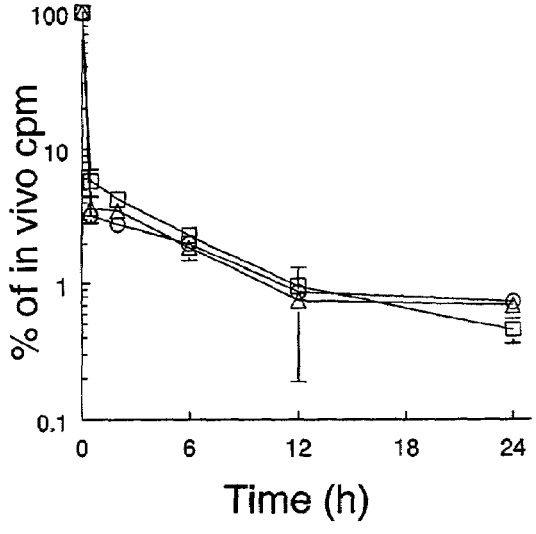

A similar observation is also seen in FIG. 9D, which shows the elimination of DOPE/CHEMS liposomes having varying content of mPEG-S-S-DSPE as a function of time. Here, the formulations were comprised of DOPE/CHEMS/mPEG-S-S-DSPE/mPEG/DSPE, 6:4:0.012:0.06 molar ratio (□); DOPE/CHEMS/mPEG-S-S-DSPE/mPEG-DSPE, 6:4:0.024:0.06 molar ratio (Δ); DOPE/CHEMS/mPEG-S-S-DSPE/mPEG-DSPE, 6:4:0.054:0.06 molar ratio (○). Again, all of the formulations have essentially the same elimination profile, with the increasing amount of cleavable PEG (mPEG-S-S-DSPE) have no measurable effect on circulation time.

In summary, circulation times increased with increasing concentration of mPEG-DSPE in either DOPE or DOPE/CHEMS liposome formulations (FIGS. 9A–9B). Approximately 5–10% of the injected liposomes still remained in the blood 24 h after injection of liposomes containing 10 mol % mPEG-DSPE. Injection of DOPE or DOPE/CHEMS liposomes that were not stabilized with mPEG-DSPE resulted in rapid clearance of the liposomes. Inclusion of from 2 to 9 mol % of mPEG-S-S-DSPE did not increase the circulation times for either the DOPE (FIG. 9C) or DOPE/CHEMS (FIG. 9D) formulations. All mPEG-S-S-DSPE formulations contained 1 mol % mPEG/DSPE to mimic the effect of adding 1 mol % coupling lipid to the formulations in targeting experiments. Increasing amounts of mPEG-S-S-DSPE in the formulations did not increase circulation half-lives of the formulations to any significant extent (FIGS. 9A–9B).

Liposomes containing mPEG-S-S-DSPE have a shorted blood circulation lifetime, relative to liposomes comprised of non-cleavable mPEG-DSPE, due to rapid cleavage of the disulfide linkage by blood components, e.g. cysteine, in vivo. The loss of steric hindrance due to the loss of PEG from the liposomes would decrease their stability in blood and increase the uptake of liposomes by the MPS. Antibody-targeted liposomes bind to and are internalized by the target cells rapidly (Lopes de Menezes et al., *J. Liposome Res.*, 9:199 (1999); Lopes de Menezes et al., *Cancer Res.*, 58:3320 (1998)). Thus, the invention contemplates administering targeted, pH-sensitive liposomes containing cleavable polymer chains to achieve binding between the targeting ligand and the target cell, internalization of the liposomes, cleavage of the polymer chains, and subsequent disruption of the lipid bilayer for release of liposomal contents intracellulary.

In vivo Therapeutic Treatment

In another study performed in support of the invention, mice were treated with targeted, pH-sensitive liposomes having releasable PEG chains. Entrapped in the liposomes was the therapeutic agent doxorubicin (DXR). As described in Example 9, the mice were treated with a single dose of 3 mg DXR/kg in free form or entrapped in liposomes. The liposome formulations are summarized in Table 2 and detailed in Example 8.

TABLE 2

Survival Time of Mice bearing CD 19± human B-lymphoma (Namalwa) cells

| Treatment Group No.[1] | Mean Survival Time (MST ± S.D. (days)) | Increased Life Span[2] (% ILS) |
|---|---|---|
| (1) Saline (MST control) | 21.0 ± 1.6 | — |
| (2) Free doxorubicin | 23.0 ± 1.4 | 9.5 |
| (3) DOPE/CHEM/mPEG-DSPE | 27.8 ± 1.6 | 32.4 |
| (4) DOPE/CHEM/mPEG-S-S-DSPE | 25.8 ± 4.0 | 22.9 |
| (5) HSPC/CHOL/mPEG-DSPE | 24.2 ± 1.3 | 15.2 |
| (6) DOPE/CHEMS/mPEG-DSPE[anti-CD19] | 42.2 ± 4.1 | 101 |
| (7) DOPE/CHEMS/mPEG-S-S-DSPE[anti-CD19] | 53.8 ± 6.5 | 156.2 |
| (8) HSPC/CHOL/mPEG-DSPE[anti-CD19] | 43.2 ± 5.7 | 105.7 |

[1]Treatment Group Nos. (3)–(8) are liposome formulations containing entrapped doxorubicin.
[2]Increased Life Span relative to mean survival time of control mice.

Table 2 shows the mean survival time for each of the treatment groups and the increased life span, calculated based on the mean survival time (MST) of the control animals. No evidence of drug toxicity was apparent in any of the test animals. Animals treated with non-targeted liposome formulations (Groups (3)–(5)) showed little improved therapeutic efficacy over the control group (P>0.05). However, the test groups treated with targeted, liposome formulations (Groups (6)–(8)) had significantly increased life spans (>100%ILS) than did the control group or groups treated with non-targeted formulations (P>0.001). Group (7) treated with DXR-DOPE/CHEMS/mPEG-S-S-DSPE/Mal-PEG-DSPE[anti-CD19] had a significantly increased %ILS compared to the other targeted treatment groups, Group 6 and Group 8.

The data presented in Table 2 and in the Figures shows that the targeted, pH-sensitive liposomes having cleavable PEG have a higher therapeutic efficacy than non-targeting or non-pH-sensitive liposomes. That is, the targeted, pH-sensitive formulations stabilized with mPEG-S-S-DSPE delivered encapsulated doxorubicin efficiently into the cytoplasm of target cells and improved the cytotoxicity of encapsulated doxorubicin in vitro, relative to a targeted formulation that lacked triggered release properties, i.e., DXR-HSPC/CHOL/mPEG-DSPE[anti-CD19]. The targeted, pH-sensitive, cleavable polymer chain formulations achieve an increased intracellular delivery of the liposome entrapped agent.

EXAMPLES

The following examples further illustrate the invention described herein and are in no way intended to limit the scope of the invention.

Materials

Hydrogenated soy phosphatidylcholine (HSPC) was obtained from Lipoid KG (Ludwigshafen, Germany), mPEG$_{2000}$-distearoylphosphatidyl-ethanolamine (mPEG2000-DSPE, also abbreviated mPEG-DSPE) can be synthesized from standard methods (Zalipsky, S., et al., in *Poly(Ethylene Glycol) Chemistry: Biotechnical and Biomedical Applications* (J. M. Harris, Ed.) Plenum Press, p. 347–370 (1992)). Doxorubicin (DXR) was purchased from Sigma Chamial Company, St. Louis, Mo. Maleimide-derivatized PEG$_{2000}$-DSPE (Mal-PEG-DSPE) (Kirpotin, D. et al., *Biochemistry*, 36:66 (1997)) was custom synthesized by Shearwater Polymers (Huntsville, Ala.). Cholesterol (CHOL) and dioleoylphosphatidylethanolamine (DOPE) were purchased from Avanti Polar Lipids (Alabaster, Ala.). N-[2-w-methoxypoly(ethylene glycol)-α-aminocarbonyl-ethyl-dithiopionyl]-DSPE (mPEG-S-S-DSPE, disulfide-linker) was synthesized as described. Sephadex G-50 and Sepharose CL-4B were purchased from Pharmacia Biotech (Uppsala, Sweden). Na$^{125}$I and cholesteryl-[1,2-[$^{3}$H](N)]-hexadecyl ether ([$^{3}$H]CHE) were purchased from Mandel Scientific (Guelph, ON). Cholesteryl hemisuccinate (CHEMS), 3-(4,5-dimethylthiazol-2-ly)-2,5-diphenyltetrazolium bromide (MTT) and iminothiolane were purchased from Sigma Chemicals (Oakville, ON). p-Xylene-bis-pyridinium bromide (DPX) and trisodium 8-hydroxypyrenetrisulfonate (HPTS) were purchased from Molecular Probes (Eugene, Oreg.). Iodination of IgG was performed according to the method described elsewhere (Lopes de Menezes et al., *Cancer Res.*, 58:3320 (1998)). Tyraminylinulin (TI) synthesis and preparation of [$^{125}$I]TI have been described previously (Sommerrnan, E. F. et al., *Biochem. Biophys. Res. Commun.*, 122:319 (1984)). The murine monoclonal antibody (mAb) anti-CD19 was prepared from the FMC-63 murine anti-CD19 hybridoma cell line obtained from Dr. H. Zola (Children's Health Research Institute, Australia). The human B-lymphoma cell line Namalwa (ATCC CRL 1432) was obtained from American Type Culture Collection (MD, USA). Human plasma was obtained from healthy volunteers at the University of Alberta, Department of Pharmacology. Nuclepore polycarbonate membranes (0.08, 0.1 and 0.2 µm pore size) were purchased from Northern Lipids (Vancouver, BC). All other chemicals were of analytical grade.

Example 1

Preparation of pH-sensitive and Non-pH-sensitive Liposomes

Sterically stabilized pH-sensitive liposomes were prepared from a mixture of dioleoylphosphatidylethanolamine (DOPE) or DOPE/CHEMS (cholesteryl hemisuccinate) and either mPEG-DSPE or mPEG-S-S-DSPE (prepared as described in Kirpotin et al.) and DSPE-PEG-maleimide (Mal-PEG-DSPE; prepared as described in U.S. Pat. No. 6,326,353) according to the lipid molar ratios of the desired formulations. The desired lipid mixture was dissolved in chloroform and dried as a thin film by rotation under reduced pressure using a rotary evaporator. The dried lipid film was hydrated by addition of an aqueous buffer to form liposomes. The liposomes were sized by sequential extrusion through a series of Nucleopore polycarbonate filters with pore size ranging from 0.2 to 0.08 µm, using a Lipex Extruder (Lipex Biomembranes, Vancouver, BC). The mean diameter of liposomes was determined by dynamic light scattering using a Brookhaven BI-90 Particle Sizer (Brookhaven Instruments, Holtsville, N.Y.). The diameters of extruded liposomes were in the range of 120±10 nm.

For liposomes loaded with either HPTS-DPX or [$^{125}$I]TI, the lipid films were hydrated with HPTS-DPX solution (30 mM HPTS, 30 mM DPX, pH 9.0, adjusted to 290 mosmol with NaCl) or [$^{125}$I]TI solution (pH 9.0). Following extrusion, the entrapped dye or [$^{125}$I]TI was removed by chromatography on Sephadex G-50 or Sepharose CL-4B columns, respectively, eluted with HEPES buffer, pH 7.4 (25 mM HEPES, 140 mM NaCl,.

The therapeutic agent, doxorubicin (DXR) was loaded by remote loading using an ammonium sulfate gradient as described in Bolotin et al. (*J. Liposome Res.*, 4:455 (1994)) with minor modification. Briefly, the lipid films were hydrated in 250 mM ammonium sulfate at pH 8.5 for formulations containing DOPE/CHEMS or a pH 9.0 for formulations containing DOPE. Minute amounts of NaOH was added to obtain complete hydration of the lipid film in some cases. Following extrusion, the external buffer was exchanged by eluting through a Sephadex G-50 column equilibrated with 10% sucrose, 25 mM Trizma base at pH 8.5 or pH 9.0 as appropriate to achieve bilayer formation. DXR was added to the pre-formed liposomes at a DXR/lipid ration of 0.2:1 (w/w), and the liposomes were incubated for 15 minutes at 22° C. The liposome-encapsulated DXR was separate from free DXR by chromatography on a Sephadex G-50 column eluted with degassed HEPES buffer. The concentration of liposome-entrapped DXR was determined by spectrophotometry ($\lambda$=490 nm) following methanol extraction. Phospholipid concentration was determined using the Fiske-Subbarow colorimetric assay (Bartlett, G. R., *J. Biol. Chem*, 234:466 (1959)).

Example 2

Antibody Coupling to Pre-Formed Liposomes

Coupling of anti-CD19 mAb to maleimide (Mal)-PEG-DSPE on the liposomes was carried out according to a previously described method (Lopes de Menezes et al., *J. Liposome Res.*, 9:199 (1999)), using $^{125}$I-labeled anti-CD19 mAb as a tracer.

Antibodies were first activated with Traut's reagent (2-iminothiolane) at a molar ratio of 20:1 (Traut's: IgG), at a concentration of 10 mg IgG/ml buffer for 1 h at 25° C. in HEPES buffer, pH 8.0 (25 mM HEPES, 140 mM NaCl). Unreacted Traut's reagent was removed using a G-50 column. The coupling reaction was run at an IgG to phospholipid molar ratio of 1:2000, under argon atmosphere for 18 h at 25° C. Uncoupled Ab was removed from the liposomes by passing the coupling mixture through a Sepharose CL-4B column in HEPES buffer, pH 7.4. The coupling efficiency was on average 80%.

All mAb densities were routinely in the range of 30–60 μg anti-CD19/μmol phospholipid for in vivo experiments and 65–80 μg anti-CD19/μmol PL for in vitro experiments.

Example 3

Leakage of Liposome-Entrapped Fluorescent Dye or Liposome-Entrapped Doxorubicin in Buffer Leakage of entrapped HPTS-DPX from various formulations of DOPE or DOPE/CHEMS liposomes was evaluated by monitoring the release of entrapped solute using a fluorescence-dequenching assay. HPTS was passively loaded into the liposomes as the water-soluble (but fluorescence-quenched) complex, HPTS-DPX. When HPTS-DPX leaks from the liposomes; it dissociated into free HPTS and DPX, increasing the HPTS fluorescence when excited at 413 nM. The DOPE and DOPE/CHEMS formulations tested were:

| Lipid Components | Molar Ratio |
|---|---|
| DOPE | 1 |
| DOPE/mPEG-DSPE | 1:0.05 |
| DOPE/mPEG-S-S-DSPE | 1:0.05 |
| DOPE/CHEMs | 6:4 |
| DOPE/CHEMS/mPEG-DSPE | 6:4:0.3 |
| DOPE/CHEMS/mPEG-S-S-DSPE | 6:4:03 |

Liposomes containing entrapped HPTS-DPX were passed over a Sephadex G-50 column immediately prior to use to remove any residual free dye or drug. Fifty (50) μl of liposomes containing entrapped dye (HPTS-DPX) or doxorubicin were incubated at 0.5 mM final PL concentration at 37° C. in 450 μl of either pH 5.5 or pH 7.4 buffers. pH sensitive liposomes containing mPEG-S-S-DSPE were also incubated with dithiothreitol (DTT) (100 nM) in both pH 5.5 or pH 7.4 buffers. At various time points, the percentage of released HPTS was determined in an aliquot of the incubation mixture by measuring the increase in sample fluorescence at an emission wavelength of 512 nm and an excitation wavelength of 413 nm (Daleke, K. et al., *Biochim. Biophys. Acta*, 1024:352 (1990)) relative to that of a pre-incubation sample (zero release) using an SLM-Aminco Model 8100 fluorimeter (Spectronic Instruments, Rochester, N.Y.); values were normalized to the increase in fluorescence obtained after lysis of a pre-incubation sample with 10% Triton X-100 (100% release) (Kirpotin et al., *FEBS Letters*, 388:115 (1996)).

The leakage of the encapsulated HPTS from DOPE and DOPE/CHEMS liposomes stabilized with either mPEG-S-S-DSPE or mPEG-DSPE in buffer at either pH 5.5 or pH 7.4 are plotted as a function of time in FIGS. 4A–4B and FIGS. 5A–5B. The results are from a representative experiment, and are means of triplicate analyses±S.D.

Example 4

Release of Liposome-Entrapped Fluorescent Dye into Cell Free Extract

Preparation of Cell Free Extract.

Namalwa cells were maintained in logarithmic growth conditions in RPMI 1640 supplemented with 10% FBS at 37° C. in a humidified atmosphere containing 5% $CO_2$. Cells ($1.0 \times 10^8$) were collected by centrifugation (1000 rpm for 10 min) and washed with 20 ml of TEA buffer (10 mM triethanolamine, 0.25 M sucrose, 10 mM acetic acid, and 1 mM EDTA, pH 7.4). The washed cells were resuspended in 4 ml TEA buffer and a protease inhibitor cocktail formulated for mammalian cell extracts (4-(2-amino-ethyl)-benzenesulfonyl fluoride, pepstatin A, trans-epoxysuccinyl-L-leucylamino (4-guanidino)butane, bestatin, leupeptin, and aprotinin; Sigma, Mo., USA) was added at 100 μl per gram of cells. The cells were ruptured at 4° C. using 40 firm strokes with a tight-fitting Dounce homogenizer. Unbroken cells were pelleted by centrifugation at 1000 rpm for 10 min at 4° C. The CFE was carefully removed from the cell pellet and then diluted to 6 ml with the addition of TEA buffer. The CFE was adjusted to pH 5.5, approximating the lysosomal pH of between 5 and 6.5 (Tycko, B. et al., *Cell*, 28:643 (1982); Tycko, B. et al., *J. Cell Biol.*, 97:1762 (1983)).

Liposomes containing HPTS-DPX were passed over a Sephadex G-50 column immediately prior to use to remove any residual free dye. The release of entrapped solute was studied using a fluorescence-dequenching assay.

Fifty (50) ml of liposomes containing entrapped dye (HPTS-DPX) were incubated at 0.5 mM final phospholipid concentration at 37° C. in 450 mL of cell free extract. The liposome formulation consisted of DOPE liposomes either not stabilized or stabilized with 3% or 5% of mPEG-S-S-DSPE, and DOPE/CHEMS liposomes either not stabilized or stabilized with 1.8 mol % or 3 mol % of mPEG-S-S-DSPE in the lipid mix. The leakage was determined as the percentage increase in the sample fluorescence over that of the pre-incubation sample treated with Triton X-100 (100% release). The result from a representative experiment slotted as a function of time is shown in FIGS. 6A–6B. Each data point is the mean of triplicate analyses±S.D.

Example 5

Leakage of Doxorubicin from pH-sensitive Liposomes Incubated in Human Plasma

The leakage of doxorubicin (DXR) in human plasma was examined for anti-CD19-targeted liposomes of DOPE/mPEG-DSPE/Mal-PEG-DSPE (1:0.04:0.01), DOPE/CHEMS/mPEG-DSPE/Mal-PEG-DSPE (6:4:0.2:01), DOPE/mPEG-S-S-DSPE/Mal-PEG-DSPE (1:0.04:0.01) are DOPE/CHEMS/mPEG-S-S-DSPE/Mal-PEG-DSPE (6:4:02:0.1).

Fifty (50) μl of liposomes containing entrapped DXR were incubated at 0.05 mM final phospholipid concentration at 37° C. in 450 μl of human plasma. At various time points, aliquots of an incubation mixture was taken and diluted in HEPES buffer (pH 7.4). The fluorescence of doxorubicin contained in liposomes was quenched due to its self-association when loaded by the ammonium sulfate method. Doxorubicin leakage was determined by fluorescence dequenching at excitation and emission wavelengths of 485 and 590 nm, respectively. Released DXR was determined as the percentage increases in the sample fluorescence over that of a pre-incubated sample treated with 10% Triton X-100% (100% release). Results of a representative experiment were plotted as a function of time are shown in FIGS. 7A–7B. Each data point is the mean of triplicate analysis.

Example 6

In vitro Cytotoxicity of Targeted, PEG-DSPE Stabilized, pH-sensitive Liposomes

A comparison of the in vitro cytotoxicity of free doxorubicin and various liposomal formulations (Table 1) was performed on Namalwa cells with an in vitro proliferation assay using a tetrazolium dye (MTT -3-(4,5-dimethylthiazol-2-yl)-2,5 diphenyltetrazolim bromide; Mosmann, J. *J. Immunol Methods*, 65:55 (1983)), as described in Lopes de Menezes et al, *Cancer Res.*, 58:3320 (1998).

Briefly, $5 \times 10^5$ Namalwa cells were plated in 96-well plates and incubated with either free DXR or various formulations of liposome-encapsulated doxorubicin with or without anti-CD19 mAb. Monoclonal antibodies were coupled to Maleimide-terminated PEG-DSPE to form liposomes having 65–80 µg mAb/µmol phospholipid. The liposomes were remotely loaded with doxorubicin at loading levels of between 140–160 µg doxorubicin/µmol phospholipid (0.24–0.28 µmol doxorubicin/µmol phospholipid). Cells were incubated for 1, 24, 48 hours at 37° C. in an atmosphere of 95% humidity and 5% $CO_2$. At the 1 hour and 24 hour incubation time periods, the cells were washed twice before replacing with fresh media and incubated for an additional 47 hours and 24 hours, respectively. All plates were incubated for a total of 48 hours. At the end of the incubation period, tetrazolium dye was added, and the plates were read on a Titertek Multiskan Plus (Flow Laboratories, Inc. Mississauga, Ontario, Canada) at dual wavelengths of 570 and 650 nm. Cytotoxicities of the various liposome formulation were expressed as mean concentration effective to inhibit cell growth by 50% ($IC_{50}$, µM DXR)±S.D. (n=3–6), and are listed in Table 1.

Example 7

Nuclear Accumulation Assay

Nuclear accumulation of doxorubicin was determined according to the method of Kirchmeier et al. (*J. Liposome Res.*, 11:15 (2001)). Briefly, $4.5 \times 10^8$/500 ml Namalwa cells, maintained under logarithmic growth conditions in RPMI 1640 supplemented with 10% FBS, were treated with either free DXR or various liposomal DXR formulations at a DXR concentration of 8 µM.

At various time points (0, 2, 4, 8, 12 hours), 100 ml of cells was pelleted by centrifugation at 1000 rpm for 10 min and washed with 20 ml of TEA buffer. Washed cells were resuspended in 3 ml TEA buffer and ruptured at 4° C. using 40 firm strokes with a tight-fitting Dounce homogenizer. Unbroken cells were pelleted and the CFE, which contained the nuclei, was carefully removed from the cell pellet. To obtain more complete homogenization, the pellet of unbroken cells was suspended in TEA buffer (3 ml) and ruptured a second time, followed again by removal of the unbroken cells. The combined supernatants were centrifuged at 1000 rpm for 10 min to remove any remaining unbroken cells. The supernatant from this centrifugation step was spun at 2000 rpm for 2.5 min at 4° C. to pellet nuclei. After removal of the supernatant, the pellet was diluted to 1 ml with TEA buffer, then vortexed and sonicated until the nuclei were evenly dispersed, as determined by visual inspection.

For each time point, three aliquots of the nuclear fractions (0.2 ml each) were placed in 1.3 ml TEA. DNA was enzymatically digested by the addition of 10 µl digitonin solution (25 mg/ml in sterile PBS, Sigma, St. Louis, Mo.), 10 µl $MgCl_2$ solution (57 mg/ml in sterile PBS) and 50 µl DNase 1 solution (3 mg/ml in sterile PBS, Sigma). Following digestion at 22° C. for 2 hours, the doxorubicin fluorescence was recorded (excitation at 480 nm and emission at 595 nm). The purity of the nuclear fraction was checked by determining the levels of enzyme markers for various cellular organelles (Lopes de Menezes et al., *J. Liposome Res.*, 9:199 (1999)).

The results are shown in FIGS. 8A–8C.

Example 8

Blood Elimination of Liposomes in BALB/c (Inbred) Mice

Female BALB/c Cr Alt B/M mice, in the weight range of 17–22 g, were obtained from University of Alberta Health Sciences Laboratory Animal Services, and were injected via the tail vein with a single bolus dose of 0.2 ml of liposomes of various formulations containing encapsulated [$^{125}$I]TI (0.5 µmol PL/mouse). The liposome formulations consisted of DOPE only, DOPE with either 3 mol %, 5 mol % or 10 mol % mPEG-DSPE, DOPE/CHEMS only and DOPE/CHEMS with 1.8 mol %, 3 mol % or 6 mol % of mPEG-DSPE; DOPE/1 mol % PEG-DSPE with either 2 mol %, 4 mol % or 9 mol % of mPEG-S-S-DSPE, and DOPE/CHEMS/mPEG-DSPE (6:4:0.06) with either 1 mol %, 2 mol % or 5 mol % of mPEG-S-S-DSPE.

At selected times post-injection, mice were anesthetized with halothane and sacrificed by cervical dislocation. A blood sample (100 µl) was collected by cardiac puncture. Blood samples, various organs and the carcass were counted for $^{125}$I label in a Beckman 8000 gamma counter. Data were analyzed using PKAnalyst (MicroMath Scientific Software).

Results from a representative experiment are shown in FIGS. 9A–9D. The data points are means of triplicate analyses±S.D.

Example 9

In vivo Administration

Namalwa cells were passaged i.p. in CB-17/ICR Tac SCID mice (Charles River Laboratories, Quebec, Canada) to develop a more virulent strain with reproducible tumor take (Lopes de Menezes et al., *Cancer Res.*, 58:3320 (1998)). Namalwa cells were harvested in sterile PBS and implanted into SCID mice. Cell viability was assessed by dye exclusion using Trypan Blue dye before and after the implantation process.

SCID mice (5 mice/group) (Charles River Laboratories), 6–8 weeks of age, were implanted with Namalwa cells i.v. ($5 \times 10^6$) and treated i.v. at 24 h after implantation with a single dose of 3 mg doxorubicin/kg as either free doxorubicin, doxorubicin-SIL[anti-CD19] or targeted DXR-loaded DOPE/CHEMS formulations stabilized with either mPEG-DSPE or mPEG-S-S-DSPE. The treatment regimens were as follows:

| Treatment Group | Formulation[1] |
| --- | --- |
| (1) | saline |
| (2) | free doxorubicin |
| (3) | liposomes composed of DOPE/CHEMS/mPEG-DSPE/ Mal-PEG-DSPE (6:4:0.24:0.06) |
| (4) | liposomes composed of DOPE/CHEMS/mPEG-S-S-DSPE/Mal-PEG-DSPE (6:4:0.24:0.06) |
| (5) | liposomes composed of HSPC/CHOL/mPEG-DSPE/ Mal-PEG-DSPE (2:1:0.08:0.02) ("DXR-SL") |
| (6) | liposomes composed of HSPC/CHOL/mPEG-DSPE/ Mal-PEG-DSPE (2:1:0.08:0.02) and 58.4 µg anti-CD19/gmol phospholipid ("DXR-SIL") |
| (7) | liposomes composed of DOPE/CHEMS/mPEG-DSPE/ Mal-PEG-DSPE (6:4:0.24:0.06) and 33.3 µg anti-CD19/µmol phospholipid |
| (8) | liposomes composed of DOPE/CHEMS/mPEG-S-S-DSPE/Mal-PEG-DSPE (6:4:0.24:0.06) and 31.2 µg anti-CD19/µmol phospholipid |

[1]All liposome formulations contained doxorubicin.

All treatment groups received 3 mg doxorubicin/kg. Mice were monitored routinely for weight loss, and euthanized as they became moribund; survival times were recorded. No evidence of drug toxicity was observed in any experimental group. All animal experiments were approved by the Health Sciences Animal Policy and Welfare Committee of the University of Alberta (Edmonton, Alberta, Canada). The mean survival time (MST) and percent increased life span (ILS) over MST of the control mice were determine and are shown in Table 2.

Although the invention has been described with respect to particular embodiments, it will be apparent to those skilled in the art that various changes and modifications can be made without departing from the invention.

It is claimed:

1. A liposome composition for intracellular delivery of a therapeutic agent, comprising
    liposomes consisting essentially of (i) a pH-sensitive lipid; (ii) between 1–20 mole percent of a lipid derivatized with a hydrophilic polymer, said polymer attached to said lipid by a bond effective to release the hydrophilic polymer in response to an existing or an induced physiologic condition; (iii) a targeting ligand; and (iv) an entrapped therapeutic agent;
    wherein said composition is adapted to bind to a target cell and to release said entrapped agent to achieve at least a two-fold increase in intracellular concentration of the agent, when compared to intracellular concentration of the agent delivered by similar liposomes lacking said releasable bond and/or said targeting ligand wherein, said releasable bond is a dithiobenzyl bond.

2. The composition of claim 1, wherein said pH-sensitive lipid is dioleoylphosphatidylethanolmaine (DOPE).

3. The composition of claim 1, wherein said liposomes further include a stabilizing component.

4. The composition of claim 3, wherein said stabilizing component is cholesteryl hemisuccinate (CHEMS).

5. The composition of claim 1, wherein said lipid derivatized polymer is phosphatidylethanolamine derivatized with polyethyleneglycol.

6. The composition of claim 1, wherein said targeting ligand an antibody or an antibody fragment.

7. The composition of claim 6, wherein said antibody fragment is selected from the group consisting of anti-CD19, anti-CD20, anti-CD22.

8. A method for increasing intracellular cytotoxicity of a liposome-entrapped agent, comprising
    providing liposomes consisting essentially of (i) a pH-sensitive lipid; (ii) between 1–20 mole percent of a lipid derivatized with a hydrophilic polymer, said polymer attached to said lipid by a bond effective to release the hydrophilic polymer in response to an existing or an induced physiologic condition; (iii) a targeting ligand; and (iv) an entrapped therapeutic agent;
    administering said liposomes to achieve (i) cleavage of the releasable bond, thereby releasing said hydrophilic polymer chain; (ii) binding of said ligand to a target cell, where said binding occurs prior to or subsequent to said cleavage; and (iii) internalization of said liposome by said target cell;
    whereby said administering is effective to achieve at least a two-fold higher intracellular cytotoxicity of said agent, relative to intracellular concentration of the agent delivered by similar liposomes lacking said releasable bond and/or said targeting ligand wherein, said releasable bond is a dithiobenzyl bond.

9. The method of claim 8, wherein cleavage of said releasable bond after said administering is achieved by naturally-occurring blood components.

10. The method of claim 8, wherein said pH-sensitive lipid is dioleoylphosphatidylethanolmaine (DOPE).

11. The method of claim 8, wherein said liposomes further include a stabilizing component.

12. The method of claim 11, wherein said stabilizing component is cholesteryl hemisuccinate (CHEMS).

13. The method of claim 8, wherein said lipid derivatized polymer is phosphatidylethanolamine derivatized with polyethyleneglycol.

14. The method of claim 8, wherein said targeting ligand an antibody or an antibody fragment.

15. The method of claim 14, wherein said antibody fragment is selected from the group consisting of anti-CD19, anti-CD20, anti-CD22.

16. A method for increasing accumulation of a therapeutic agent into cellular nuclei, comprising
    providing liposomes consisting essentially of (i) a pH-sensitive lipid; (ii) between 1–20 mole percent of a lipid derivatized with a hydrophilic polymer, said polymer attached to said lipid by a bond effective to release the hydrophilic polymer in response to an existing or an induced physiologic condition; (iii) a targeting ligand; and (iv) an entrapped therapeutic agent;
    administering said liposomes to achieve (i) cleavage of the releasable bond, thereby releasing said hydrophilic polymer chain; (ii) binding of said ligand to a target cell, where said binding occurs prior to or subsequent to said cleavage; and (iii) internalization of said liposome by said target cell;
    whereby said administering is effective to achieve at least a two-fold higher accumulation of said agent in the nucleus of the target cell, when compared to intracellular concentration of the agent delivered by similar liposomes lacking said releasable bond and/or said targeting ligand wherein, said bond is a dithiobenzyl bond.

17. The method of claim 16, wherein cleavage of said releasable bond after said administering is achieved by naturally-occurring blood components.

18. The method of claim 16, wherein said pH-sensitive lipid is dioleoylphosphatidylethanolmaine (DOPE).

19. The method of claim 16, wherein said liposomes further include a stabilizing component.

20. The method of claim 19, wherein said stabilizing component is cholesteryl hemisuccinate (CHEMS).

21. The method of claim 16, wherein said lipid derivatized polymer is phosphatidylethanolamine derivatized with polyethyleneglycol.

22. The method of claim 16, wherein said targeting ligand an antibody or an antibody fragment.

23. The method of claim 22, wherein said antibody fragment is selected from the group consisting of anti-CD19, anti-CD20, anti-CD22.

* * * * *